United States Patent
Cohen et al.

(10) Patent No.: US 8,552,041 B2
(45) Date of Patent: Oct. 8, 2013

(54) THERAPEUTIC APPROACHES FOR TREATING ALZHEIMER DISEASE AND RELATED DISORDERS THROUGH A MODULATION OF CELL STRESS RESPONSE

(75) Inventors: Daniel Cohen, Le Vesinet (FR); Ilya Chumakov, Vaux le Penil (FR); Serguei Nabirochkin, Chatenay Malabry (FR); Oxana Guerassimenko, Milly-la-Foret (FR)

(73) Assignee: Pharnext, Paris (FR)

( * ) Notice: Subject to any disclaimer, the term of this patent is extended or adjusted under 35 U.S.C. 154(b) by 164 days.

(21) Appl. No.: 12/915,689

(22) Filed: Oct. 29, 2010
(Under 37 CFR 1.47)

(65) Prior Publication Data

US 2012/0071483 A1    Mar. 22, 2012

Related U.S. Application Data

(63) Continuation-in-part of application No. PCT/EP2009/055207, filed on Apr. 29, 2009.

(60) Provisional application No. 61/048,585, filed on Apr. 29, 2008.

(51) Int. Cl.
  *A61K 31/137* (2006.01)
  *A61K 31/42* (2006.01)
  *A61P 25/28* (2006.01)

(52) U.S. Cl.
  USPC .......................................... 514/379; 514/380

(58) Field of Classification Search
  USPC .................................................. 514/379, 380
  See application file for complete search history.

(56) References Cited

U.S. PATENT DOCUMENTS

| 5,567,720 A * | 10/1996 | Averback ..................... 514/345 |
| 7,034,182 B2 * | 4/2006 | Fang et al. ..................... 564/147 |
| 2005/0020634 A1 * | 1/2005 | Terashita et al. .............. 514/337 |

FOREIGN PATENT DOCUMENTS

| EP | 1777225 | 4/2007 |
| WO | WO 03/037381 | 5/2003 |
| WO | WO 03/061767 | 7/2003 |
| WO | WO 2006/003492 | 1/2006 |
| WO | WO 2008/027993 | 3/2008 |
| WO | WO 2008/039514 | 4/2008 |

OTHER PUBLICATIONS

*International Search Report*; PCT Application No. PCT/EP2009/055207, mailed Sep. 21, 2009 (3 pages).

* cited by examiner

*Primary Examiner* — Renee Claytor
*Assistant Examiner* — Sahar Javanmard
(74) *Attorney, Agent, or Firm* — Cesari and McKenna LLP

(57) ABSTRACT

The present invention relates to compositions and methods for the treatment of Alzheimer's disease and related disorders. More particularly, the invention relates to combined therapies that modulate cell stress response for treating said disease.

2 Claims, 6 Drawing Sheets

THERAPEUTIC APPROACHES FOR TREATING ALZHEIMER DISEASE AND RELATED DISORDERS THROUGH A MODULATION OF CELL STRESS RESPONSE

CROSS REFERENCE TO RELATED APPLICATION

This application is a continuation-in-part of PCT Application No. PCT/EP2009/055207, filed on Apr. 29, 2009, which is a non-provisional of U.S. Provisional Application No. 61/048,585, filed on Apr. 29, 2008, the contents of both of the foregoing applications are hereby incorporated by reference in their entirety.

BACKGROUND OF THE INVENTION

The present invention relates to compositions and methods for the treatment of Alzheimer's disease (AD) and related disorders.

AD is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (ability to recognize objects, persons, sounds, shapes, or smells) attributable to involvement of the cortical association areas. Special symptoms such as spastic paraparesis (weakness affecting the lower extremities) can also be involved (1-4).

Incidence of Alzheimer disease increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis (5).

The incidence rate of AD increases dramatically with age. United Nation population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources (6).

Memory impairment is the early feature of the disease and involves episodic memory (memory for day-today events). Semantic memory (memory for verbal and visual meaning) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of Alzheimer's disease is sufficiently characteristic to allow identification in approximately 80% of cases (7). Nevertheless, clinical heterogeneity does occur and not only is this important for clinical management but provides further implication of specific medication treatments for functionally different forms. (8).

The pathological hallmark of AD includes amyloid plaques containing beta-amyloid (Abeta), neurofibrillary tangles (NFT) containing Tau and neuronal and synaptic dysfunction and loss (9-11). For the last decade, two major hypotheses on the cause of AD have been proposed: the "amyloid cascade hypothesis", which states that the neurodegenerative process is a series of events triggered by the abnormal processing of the Amyloid Precursor Protein (APP) (12), and the "neuronal cytoskeletal degeneration hypothesis" (13), which proposes that cytoskeletal changes are the triggering events. The most widely accepted theory explaining AD progression remains the amyloid cascade hypothesis (14-16) and AD researchers have mainly focused on determining the mechanisms underlying the toxicity associated with Abeta proteins. On contrary, Tau protein has received much less attention from the pharmaceutical industry than amyloid, because of both fundamental and practical concerns. Moreover, synaptic density change is the pathological lesion that best correlates with cognitive impairment than the two others. Studies have revealed that the amyloid pathology appears to progress in a neurotransmitter-specific manner where the cholinergic terminals appear most vulnerable, followed by the glutamatergic terminals and finally by the GABAergic terminals (11).

SUMMARY OF INVENTION

The purpose of the present invention is to provide new therapeutic approaches for treating AD and related disorders.

The inventors have identified a molecular pathway which is involved in the genesis of AD and offers novel targets for development of new treatments to ameliorate AD and related disorders, particularly for the development of combination therapies using novel or existing molecules previously used in other indications. More particularly, the inventors have identified several drugs which, alone or in combination(s), can effectively affect such pathway and represent a new and effective therapy for the treatment of AD and related disorders.

The invention therefore provides novel compositions and methods for treating AD disease and related disorders.

More particularly, the invention relates to compositions suitable for treating Alzheimer's disease or a related disorder in a subject in need thereof, wherein said compositions comprise a drug that inhibits cell stress response.

A further object of this invention relates to compositions suitable for treating Alzheimer's disease or a related disorder in a subject in need thereof, wherein said compositions comprise a combination of at least two drugs that inhibit cell stress response, for combined, separate or sequential administration.

More preferably, the drug or drugs that inhibit cell stress response bind to or modulate the activity of a protein encoded by a gene selected from ACCN1, ADRA1A, ADRB2, AFADIN, AKT, ALDH2, ALOX12, AMPK, APBA1, APBA2BP, APG1, APG12, APOER2, ATG5, ATG7, ATM, ATP1A1, ATP2A3, ATP2B1, ATP6V1C1, ATR, BACE1, BAD, BAX, BCAR1, BCL2, BECLIN1, BK channels (KCNMA1, KCNMB1), BRCA1, CACNA1C, CALCINEURIN, CD36, CD44, CDH1, CDH2, CDK5, CDKN1A, CHK1, CHRM1, CHRM2, CHRM3, CHRM4, CHRM5, CK1, CTNNA2, CTNNB1, CULLIN1, CYCLINE, DCC, DGKB, DGKH, DNAJB9, DOCK3, DRD2, EDNRA, ELAVL2, ERK1, ERK2, EZRIN, FAS, FKBP12, FKBP12.6, FOXO3A, FZ2, GADD45, GNPTAB, GPC5, GRK2, GRK5, GRP170, GRIN2B, GRIN3A, GSK3B, HAS1, HAS2, HAS3, HIPK2, HSPA5, HSP90B1, HSPA5, HTR1A, IDE, IMPDH1, IMPDH2, INS, INSR, IRF1, ITB1, ITGA1, ITGB1, ITPR1, JNK1, LAMA1, MAD1L1, MAO, MCC1, MDM1, MME, MOESIN, MTOR, NADPH OXIDASE, NEDD9, NETRIN1, NFKB1, NHERF, NOS1, NOS2A, NOS3, PAELR, PAK1, PARK2, PCAF, PDE11A, PDE3A, PDE4D, PDE5, PDE6D, PI3K, PIK3C3, PKCA, PLCB1, PLD2, PLN, PML, POP2, PRDX5, PRDX6, PRKG1, PTPRG, PTPRM, PVRL1, RAC1, RACK1, RADIXIN, RHOA, ROR2, RTN1, RYR3, SAPK3, SCN1A, SCN1B, SCNN1D, SCNN1G, SH3BP5, SILL SLC8A1, SLC8A2, SLC8A3, SLN, SNCA, SNCAIP, SORBS2, SORCS2, SRC, SYN1, THBS2, TP53, TP63, TRPC3, TRPC4, TRPC5, UNC5C, VPS15, WNT1A, WNT5A, WWOX, XANTHINE OXIDASE, and YES1.

Specific and preferred examples of such drugs include, without limitation, compounds selected from acamprosate, albuterol, alendronate, amlodipine, arabitol, cilostazol, dasatinib, fosphenyloin, leflunomide, levosimendan, mannitol, metaraminol, methimazole, milrinone, nitroprusside, omeprazole, phenformin, sodium phenylbutyrate, prilocalne, rapamycin, rifabutin, sulfisoxazole, tadalafil, terbinafine, thioguanine, trehalose, vidarabine and zonisamide, or a combination thereof.

A specific object of this invention relates to a composition for treating Alzheimer's disease or a related disorder in a subject in need thereof, wherein said composition comprises at least sulfizoxazole.

In a particular embodiment, the compositions of this invention further comprise at least one drug that modulates angiogenesis, for combined, separate or sequential use.

Alternatively, or in addition, the compositions of this invention may further comprise at least one drug that modulates synapse function, for combined, separate or sequential use.

The compositions of this invention typically further comprise a pharmaceutically acceptable carrier or excipient.

A further object of this invention resides in a method of producing a drug for treating Alzheimer's disease or a related disorder, the method comprising a step of testing a candidate drug for activity on cell stress response and selecting candidate drugs that inhibits cell stress response.

The invention also relates to a method of producing a composition for treating Alzheimer's disease or a related disorder, the method comprising preparing a combination of a drug that inhibits cell stress response and a drug that modulates angiogenesis or synapse function, and formulating said combination of drugs for simultaneous, separate or sequential administration thereof to a subject in need thereof.

The invention further relates to a method of treating Alzheimer's disease or a related disorder, the method comprising simultaneously, separately or sequentially administering to a subject in need thereof a drug or a combination of drugs that inhibit cell stress response.

The invention further relates to a method of treating Alzheimer's disease or a related disorder, the method comprising simultaneously, separately or sequentially administering to a subject in need thereof a drug that inhibits cell stress response and a drug that modulates angiogenesis and/or a drug that modulates synapse function.

The invention further relates to the use of a drug that inhibits cell stress response for the manufacture of a medicament for treating Alzheimer's disease or a related disorder.

The invention further relates to the use of a combination of at least two drugs that inhibit cell stress response for the manufacture of a medicament for treating Alzheimer's disease or a related disorder, wherein said at least two drugs are administered together, separately or sequentially.

As discussed in the present application, the above therapies and combination therapies provide novel and effective approaches for treating AD in human subjects.

DETAILED DESCRIPTION OF THE INVENTION

Figure 1:
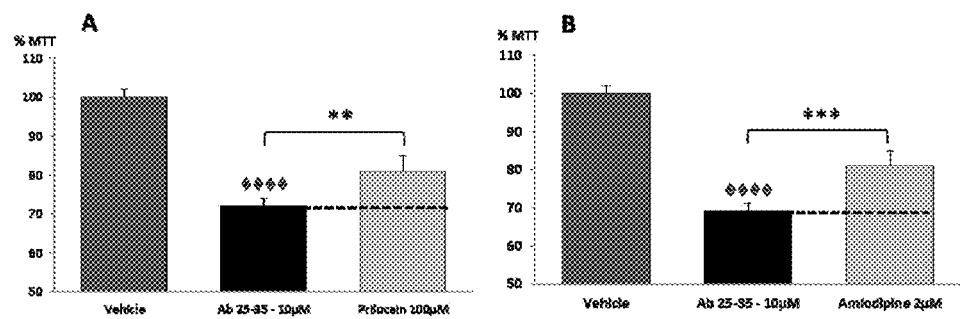
FIG. 1: Effect of selected drugs on NGF-differentiated PC12 viability after beta-amyloid intoxicated intoxication. ◊◊◊◊◊: $p<0.00001$: significantly different from vehicle. :$p<0.01$; *:$p<0.0001$: significantly different from Abeta$_{25-35}$. Bilateral Student's t test. Abeta$_{25-35}$ 10 µM produces a significant intoxication, above 25%, compared to vehicle-treated neurons (FIGS. 1-A and B). This intoxication is significantly prevented by Prilocaln (FIG. 1A) or Amlodipine (FIG. 1B).

The present invention provides new therapeutic approaches for treating AD or related disorders. The invention discloses novel use of drugs or drug combinations which allow an effective correction of such diseases and may be used for patient treatment.

The term "AD related disorder" designates Alzheimer's disease (AD), senile dementia of AD type (SDAT), Parkinson's disease, Lewis body dementia, vascular dementia, mild cognitive impairment (MCI), age-associated memory impairment (AAMI) and problem associated with ageing, post-encephalitic Parkinsonism, ALS and Down syndrome.

As used herein, "treatment" of a disorder includes the therapy, prevention, prophylaxis, retardation or reduction of symptoms provoked by the disorder. The term treatment includes in particular the control of disease progression and associated symptoms.

The term "inhibit", as it refers to cell stress response ("CSR"), includes any reduction in the CSR as compared to the existing activity in the subject. Such reduction may include a partial diminution, e.g., from 5-20%, which is sufficient to improve the patient condition, as well as more substantial reductions, e.g., from 20-50% or more complete inhibition, e.g., above 50%. The inhibition can be evaluated or verified using known biological tests, such as described in the experimental section.

Also, the designation of specific compounds within the context of this invention is meant to include not only the specifically named molecules, but also any pharmaceutically acceptable salt, hydrate, ester, ether, isomers, racemate, conjugates, or pro-drugs thereof.

The term "combination" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

As discussed above, the invention relates to compositions and methods for treating Alzheimer's disease or a related disorder in a subject in need thereof, using a drug or a combination of drugs that inhibits cell stress response.

By a comprehensive integration of experimental data covering results of cell biology studies, expression profiling experiments and genetic association studies, describing different aspects of Alzheimer's disease and links existing in cellular signalling and functional pathways, the inventors have uncovered that cell stress response represents a important mechanism which is altered in subjects having AD. Genes located in said functional network and implicated in Alzheimer's disease were selected by the following criteria:
 (1)—direct interaction with the genes causatively responsible for familial cases of Alzheimer's disease (APP, ApoE, presenilins, tau protein),
 (2)—functional partners of the genes selected by the criterion (1),
 (3)—nearest functional partners of the genes selected by the criterion (2).

Through this process, the inventors were able to establish that the network responsible for cell stress response is a major functional network affected in Alzheimer's disease.

The inventors have more specifically established that cell stress response is a functionally-relevant hallmark of Alzheimer's disease. As discussed below, the inventors have identified three families of proteins, within the cell stress response network, which are functionally relevant to the genesis and control of Alzheimer's disease, and represent valuable targets for (combination) therapies. These groups of proteins are, more specifically, proteins participating in calcium homeostasis, in protein folding, and in execution of apoptosis.

In a particular embodiment, the present invention more specifically relates to compositions and methods using a drug or drug combination that modulates the activity of a protein involved in calcium homeostasis.

Calcium, one of the most important intracellular messengers, mediates a pleiotropy of cellular processes in both neuronal and endothelial cells, including synaptic plasticity, angiogenesis and apoptosis. Mutations, abnormal folding or hyperphosphorylation of presenilin, APP and tau proteins affect calcium homeostasis. Reciprocally, disruption of intracellular calcium signalling exacerbates characteristic lesions of Alzheimer disease leading to accelerated accumulation of β-amyloid aggregations and hyperphosphorylation of tau protein, indicating existence of regulatory feed-back between calcium homeostasis and AD-specific cellular pathology.

Intracellular calcium level is precisely regulated by cooperative action of a series of calcium permeable channels, calcium pumps and calcium exchangers in plasma membrane and endoplasmatic reticulum. For instance, calcium is dynamically stored in the endoplasmic reticulum (ER), which is able to accumulate very high $Ca^{2+}$ levels due to activity of $Ca^{2+}$ SERCA pumps, reaching millimolar concentrations (17). Release of Ca2+ from endoplasmatic reticulum is controlled by two types of $Ca^{2+}$ release channels, namely the Ryanodine Receptors (RYR) and the IP3 Receptors (ITPR). They could be directly activated by multiple signalling messengers, including local cytoplasmic fluctuation of Ca2+ concentrations or IP3, and are functionally modulated by several regulatory proteins like PKA, PRKG1, mTOR, calcineurin, FKBP, phospholamban etc. (18). The SERCA pumps are regulated by $Ca^{2+}$ concentration within ER, when lowered calcium ER content increases SERCA activity. At the level of plasma membrane, calcium homeostasis is mainly regulated by store-operated and voltage-gated calcium channels responsible for the Ca2+ entry, calcium extruding ATPase pumps, $Na^+/Ca2+$ exchangers and voltage-gated $Na^+$ channels.

We identified a network of genes implicated in calcium homeostasis pathway, whose function could be modified by mutant presenilin proteins or by toxic β-amyloid. Among them, IP3R (ITPR1) and RYR3 receptors, ATP2A3 (SERCA3 Ca2+ATPase) regulating calcium homeostasis on the level of ER, plasma membrane ATPase ATP2B1, extruding calcium ions from eukaryotic cells against concentration gradients, and voltage-gated Na+ channels represent particular interest. It was shown that APP, Aβ42 and mutated PS1 are able to modulate activity of ryanodine receptors and SERCA pumps. Aβ42 and FAD-variant of PS1 increase RYR3 expression and activity (19-21) leading to enhanced neuronal vulnerability to glutamate excitotoxic insult (22). Moreover, inhibition of calcium reuptake through SERCA pump correlates with decrease of Abeta release, while promoting SERCA activity enhances Abeta production (23). Further, at the level of plasma membrane, presenilin and BACE-1 are involved in processing of β-subunits of voltage-gated sodium channels, which modulate and could—under pathological conditions—reverse activity of Na+/Ca2+ exchangers provoking excessive intracellular calcium accumulation (24).

In another particular embodiment, the present invention more specifically relates to compositions and methods using a drug or drug combination that modulates the activity of a protein involved in protein folding or aggregation.

Protein aggregation is a central cytopathological phenomenon in AD. Two major cellular hallmarks of Alzheimer's disease are manifested in development of neurofibrillary tangles (NFTs) and deposition of amyloid plaques, composed of aggregated hyperphosphorylated tau protein and Aβ fragments of APP protein respectively. Another protein prone to aggregation—α-synuclein, recognized as rather specific hallmark of Parkinson Disease, can be nevertheless detected in amyloid plaques in most cases of sporadic and familial forms of Alzheimer's disease (25-26).

We identified pathway of several genes implicated in modulation of folding, posttranslational modification and processing of every major constituent of Alzheimer's disease-associated protein's aggregations. This finding underlines importance of combined pathological effect of misfolded tau, Abeta and synuclein proteins for development of Alzheimer's disease. For instance, we identified insulin-degragating enzyme IDE, which is also involved in proteolysis of Abeta, (27) and APBA1 and APBA2BP proteins that interact with APP and regulate its stability and functions (28-29). As well, data mining revealed α-synuclein (SNCA), its interacting partner Synphilin (SNCAIP) and PARK2, an ubiquitin-protein ligase implicated in SNCA clearance and protection of neurons against α-synuclein toxicity, as risk factors for development of Alzheimer's disease (30).

Imbalance in the activity of kinases such as GSK3β, CDK5 and MARK (31-32) and phosphatases regulating phosphorylation level of tau protein could contribute to and intensify tau aggregation. Given that presenilin is also functionally regulated by the GSK-3β-dependent phosphorylation, the GSK-3β kinase might play a particularly important role in pathogenesis of Alzheimer disease. This conclusion is re-enforced by our finding that a few signalling modules regulating GSK-33 kinase activity or its direct interaction with tau protein—WWOX (33), hyaluronan CD44 receptor, Wnt receptors Fz2/ROR2 and insulin receptor/PTPRG phosphatase complex (34)—could be associated with genesis of Alzheimer's disease.

In a further particular embodiment, the present invention relates to compositions and methods using a drug or drug combination that inhibits apoptosis.

Apoptosis, recognized as a major cellular mechanism responsible for cellular loss in Alzheimer's disease, can be effectively triggered by cellular insults typically associated with development of Alzheimer disease—disrupted calcium homeostasis and increased production of reactive oxygen species (ROS) stimulated by toxic aggregates of the β-amyloid peptide (Abeta).

As identified by our analysis, apoptosis in the case of Alzheimer disease, most likely, is executed through canonical p53-dependent pathways. p53 is a DNA-binding protein and works as a transcription factor that control expression of target genes inhibiting growth and invasion of tumour cells. Therefore, p53 is recognized as a tumour suppressor protein and plays an essential role in the regulation of cell cycle progression, specifically in the transition from G0 to G1 and G2/M DNA damage check-point, and apoptosis induction. The latter seems to be mediated either by stimulation of pro-apoptotic proteins expression, such as Bax, or by repression of anti-apoptotic proteins expression such as Bcl-2.

The p53 protein can be regulated through post-translational modifications and through interactions with positive and negative regulatory factors. We have identified several such regulatory proteins—WWOX, MDM1, HIPK2 and PML—confirming the proposal about the pivotal role of the p53 protein in cell death execution in Alzheimer's disease. A p53-interacting WW domain-containing oxidoreductase (WOXW) is an essential mediator of the TNFα cytotoxicity and mediates apoptosis synergistically with p53 (35). Homeodomain-interacting nuclear serine/threonine protein kinase-2 (HIPK2) phosphorylates p53 at Ser 46 and cooperates with p53 in the activation of p53-dependent transcription and apoptotic pathways (36). Finally, the PML protein antagonizes effect of MDM2 protein, which promotes p53 degradation by the proteasome, and activates p53 by recruiting it to multiprotein complexes termed PML-nuclear bodies (37).

Among the receptor systems that could be directly and specifically implicated in induction of apoptosis in context of Alzheimer disease, UNC5C (Unc-5 Homolog C) and DCC (Deleted in Colorectal Carcinoma) netrin receptors, involving in axon guidance and angiogenesis, represent particular interest. These receptors are designated putative conditional tumor suppressors, since they behave as netrin-dependent receptors inducing apoptosis in the absence of their ligand (38). Binding of netrin-1 to these receptors inhibits tumour suppressor p53-dependent apoptosis, and p53 is directly involved in transcriptional regulation of netrin-1 and its receptors (39). Moreover, the DCC receptor is processed by presenilin to generate intracellular receptor domain possessing transcriptional activity (40). Thus, our data mining suggests that netrin receptors-mediated and p53-dependent apoptosis could be one of the specific pro-apoptotic pathways implicated in pathological cell loss in context of Alzheimer disease, in addition to rather unspecific pro-apoptotic programs stimulated by disrupted calcium homeostasis and excessive ROS production.

In a particular embodiment, the present invention more specifically relates to compositions and methods using a drug combination that inhibits the activity of at least two distinct proteins involved in calcium homeostasis, in protein folding, and in execution of apoptosis.

In the present invention, the inventors propose novel compositions, which can be used to inhibit cell stress response induced in Alzheimer's disease and other neurogenerative disorders.

In a particular embodiment, the compositions and methods of this invention use drugs that inhibit cell stress response through their interaction with or modulation of one gene or protein as listed above.

More specifically, the compositions of this invention comprise a drug or drugs that inhibit cell stress response through the binding to or modulation of the activity of a protein encoded by a gene selected from ACCN1, ADRA1A, ADRB2, AFADIN, AKT, ALDH2, ALOX12, AMPK, APBA1, APBA2BP, APG1, APG12, APOER2, ATG5, ATG7, ATM, ATP1A1, ATP2A3, ATP2B1, ATP6V1C1, ATR, BACE1, BAD, BAX, BCAR1, BCL2, BECLIN1, BK channels (KCNMA1, KCNMB1), BRCA1, CACNA1C, CALCINEURIN, CD36, CD44, CDH1, CDH2, CDK5, CDKN1A, CHK1, CHRM1, CHRM2, CHRM3, CHRM4, CHRM5, CK1, CTNNA2, CTNNB1, CULLIN1, CYCLINE, DCC, DGKB, DGKH, DNAJB9, DOCK3, DRD2, EDNRA, ELAVL2, ERK1, ERK2, EZRIN, FAS, FKBP12, FKBP12.6, FOXO3A, FZ2, GADD45, GNPTAB, GPC5, GRK2, GRK5, GRP170, GRIN2B, GRIN3A, GSK3B, HAS1, HAS2, HAS3, HIPK2, HSPA5, HSP90B1, HSPA5, HTR1A, IDE, IMPDH1, IMPDH2, INS, INSR, IRF1, ITB1, ITGA1, ITGB1, ITPR1, JNK1, LAMA1, MAD1L1, MAO, MCC1, MDM1, MME, MOESIN, MTOR, NADPH OXIDASE, NEDD9, NETRIN1, NFKB1, NHERF, NOS1, NOS2A, NOS3, PAELR, PAK1, PARK2, PCAF, PDE11A, PDE3A, PDE4D, PDE5, PDE6D, PI3K, PIK3C3, PKCA, PLCB1, PLD2, PLN, PML, POP2, PRDX5, PRDX6, PRKG1, PTPRG, PTPRM, PVRL1, RAC1, RACK1, RADIXIN, RHOA, ROR2, RTN1, RYR3, SAPK3, SCN1A, SCN1B, SCNN1D, SCNN1G, SH3BP5, SILL SLC8A1, SLC8A2, SLC8A3, SLN, SNCA, SNCAIP, SORBS2, SORCS2, SRC, SYN1, THBS2, TP53, TP63, TRPC3, TRPC4, TRPC5, UNC5C, VPS15, WNT1A, WNT5A, WWOX, XANTHINE OXIDASE, and YES1.

The sequences of all of the above listed genes and proteins are available from gene libraries and can be isolated by techniques known in the art. Furthermore, the activity of these genes and proteins can be assessed by techniques known per se in the art, as discussed in the experimental section.

The invention further describes drugs that can be used to modulate these target genes and proteins. The invention discloses the identification and activity of particular drugs which, either alone but preferentially in combination(s), modulate the above pathway and may be used to treat said diseases. In particular, we identified small molecules which already exist in the literature but being used to treat distinct diseases in human subjects.

In this respect, in a most preferred embodiment, the compositions of this invention comprise at least a modulator of AMPK (preferably selected from phenformin and vidarabine), an inhibitor of ATP1A1 (preferably, omeprazole), an inhibitor of CACNA1C (preferably, amlodopine), an antagonist of EDNRA endothelin receptor (preferably, sulfisoxazole), a modulator of GABAergic and glutamatergic GRIN2B and GRIN3A receptors (preferably, acamprosate), an inhibitor of GSK3B activity (preferably selected from albuterol and metaraminol), a modulator of HAS1-3 hyaluronan synthases (preferably, leflunomide), an inhibitor of IMPDH1 and IMPDH2 (preferably, thioguanine), an inhibitor of MTOR (preferably, rapamycin), an inhibitor of PDE11A, PDE4A and PDE5A phosphodiesterases (preferably, tadalafil), an inhibitor of PDE3A (preferably, cilostazol), an inhibitor of PDE4D (preferably, milrinone), a modulator of PRDX5 and PRDX6 (preferably, methimazole), an activator of PRKG1 (preferably selected from nitroprusside, tadalafil and cilostazol), a modulator of RHOA (preferably selected from alendronate and terbinafine), a modulator of RYR3 (preferably, prilocalne), an inhibitor of SCN1A and an activator of BK channels (preferably, zonisamide), an inhibitor of SCN1A/B (preferably selected from zonisamide and fosphenyloin), an inhibitor of YES1 and SRC (preferably, dasatinib), an activator of autophagy (preferably, trehalose), and/or chemical chaperons (preferably selected from sodium phenylbutyrate, rifabutin, arabitol and mannitol).

As discussed above, the invention particularly proposes to design combination therapies to address the mechanisms of AD and related disorders. In this respect, examples of most preferred target and drug combinations are disclosed below. More preferably, the composition comprises at least one of the following combinations of drugs, for combined, separate or sequential administration:

a modulator of AMPK (preferably, phenformin) and an inhibitor of sodium channel SCN1A and an activator of BK channels (preferably, zonisamide), a modulator of GABAergic and glutamatergic receptors (preferably, acamprosate) and a modulator of RHOA (preferably, terbinafine), an inhibitor of sodium channel SCN1A and an activator of BK channels (preferably, zonisamide) and a modulator of RYR3 ryanodine receptor (preferably, prilocalne), a modulator of AMPK (preferably, phenformin) and a modulator of RYR3 ryanodine receptor (preferably, prilocalne), a modulator of AMPK (preferably, phenformin) and a modulator of RHOA (preferably, terbinafine), an inhibitor of sodium channel SCN1A and an activator of BK channels (preferably, zonisamide) and a modulator of RHOA (preferably, terbinafine), a modulator of RYR3 ryanodine receptor (preferably, prilocalne) and a modulator of RHOA (preferably, terbinafine).

a modulator of AMPK (preferably, phenformin) and a chemical chaperon (preferably, rifabutin), an inhibitor of sodium channel SCN1A and an activator of BK channels (preferably, zonisamide) and chemical chaperon (preferably, rifabutin), a modulator of RYR3 ryanodine receptor (preferably, prilocalne) and a chemical chaperon (preferably, rifabutin), a modulator of RHOA (preferably, terbinafine) and a chemical chaperon (preferably, rifabutin), or a modulator of AMPK (preferably, phenformin) and an inhibitor of PDE11A and PDE4A, PDE5A phosphodiesterases (preferably, tadalafil).

Most preferred examples of compositions of this invention comprise a compound selected from acamprosate, albuterol, alendronate, amlodipine, arabitol, cilostazol, dasatinib, fosphenyloin, leflunomide, levosimendan, mannitol, metaraminol, methimazole, milrinone, nitroprusside, omeprazole, phenformin, sodium phenylbutyrate, prilocalne, rapamycin, rifabutin, sulfisoxazole, tadalafil, terbinafine, thioguanine, trehalose, vidarabine and zonisamide, or a combination thereof.

In another preferred embodiment, the compositions of the invention comprise at least one compound chosen from the group consisting of acamprosate, cilostazol, methimazole, phenformin, prilocalne, tadalafil, terbinafine, zonisamide and rifabutin, or salts or prodrugs or derivatives or sustained release formulations thereof.

In a specific and preferred embodiment, the composition of the invention, comprises at least sulfisoxazole, or a salt, prodrug, derivative, or sustained release formulation thereof, for treating Alzheimer's disease (AD) in a subject in need thereof.

In another specific and preferred embodiment, the composition of the invention, comprises at least tadalafil, or a salt, prodrug, derivative, or sustained release formulation thereof, for treating Alzheimer's disease (AD) in a subject in need thereof.

In another preferred embodiment, the compositions of the invention comprise a combination of at least two compounds chosen from the group consisting of acamprosate, cilostazol, levosimendan, methimazole, phenformin, prilocalne, tadalafil, terbinafine, zonisamide and rifabutin, or salts or prodrugs or derivatives or sustained release formulations thereof, for simultaneous, separate or sequential administration.

In another embodiment, the compositions according to the invention comprise a combination of at least two compounds chosen from the group consisting of acamprosate, cilostazol, methimazole, phenformin, prilocalne, tadalafil, terbinafine, zonisamide and rifabutin, or salts or prodrugs or derivatives or sustained release formulations thereof, wherein said composition inhibits cell stress response induced in neurodegenerative disorders selected from the group consisting of Alzheimer's disease (AD), Parkinson's disease (PD), Amyotrophic lateral sclerosis (ALS) and multiple sclerosis (MS).

In another preferred embodiment, the compositions of the invention comprise a combination of at least two compounds chosen from the group consisting of acamprosate, cilostazol, levosimendan, methimazole, phenformin, prilocalne, tadalafil, terbinafine, zonisamide and rifabutin, or salts or prodrugs or derivatives or sustained release formulations thereof, for treating Alzheimer's disease (AD).

In this regard, the preferred composition for treating Alzheimer's disease comprises sulfisoxazole in combination with at least one compound chosen from the group consisting of acamprosate, amlodipine, cilostazol, leflunomide, levosimendan, methimazole, phenformin, prilocalne, tadalafil, terbinafine, zonisamide and rifabutin, or salts or prodrugs or derivatives or sustained release formulations thereof.

Preferably, the compositions for treating Alzheimer's disease or a related disorder in a subject in need thereof, comprise at least one of the following drug combination for combined, separate or sequential administration:
phenformin and zonisamide,
acamprosate and terbinafine,
zonisamide and prilocalne,
phenformin and prilocalne,
phenformin and terbinafine,
zonisamide and terbinafine,
prilocalne and terbinafine,
phenformin and rifabutin,
zonisamide and rifabutin,
prilocalne and rifabutin,
terbinafine and rifabutin,
phenformin and tadalafil,
sulfisoxazole and zonisamide,
sulfisoxazole and terbinafine, or
sulfisoxazole and levosimendan.

Each of the above specific drug combinations represents per se a particular object of the present invention.

In the most preferred embodiment, the composition according to the invention comprises at least amlodipine and prilocalne, or salts or prodrugs or derivatives or sustained release formulations thereof, for simultaneous, separate or sequential administration.

In another preferred embodiment, the composition of the invention comprises at least amlodipine and/or prilocain, or salts or prodrugs or derivatives or sustained release formulations thereof, for treating Alzheimer's disease or related disorder. In another particular embodiment, the composition of the invention further comprises at least one drug that inhibit cell stress response, for combined, separate or sequential use.

Preferably, that additional drug that inhibit cell stress response is selected from a modulator of AMPK (preferably, vidarabine), an inhibitor of ATP1A1 (preferably, omeprazole), an inhibitor of GSK3B activity (preferably selected from albuterol and metaraminol), an inhibitor of IMPDH1 and IMPDH2 (preferably, thioguanine), an inhibitor of MTOR (preferably, rapamycin), an inhibitor of PDE4D (preferably, milrinone), an activator of PRKG1 (preferably, cilostazol), a modulator of RHOA (preferably, alendronate), an inhibitor of SCN1A/B (preferably, fosphenyloin), an inhibitor of YES1 and SRC (preferably, dasatinib), an activator of autophagy (preferably, trehalose), and/or chemical chaperons (preferably selected from sodium phenylbutyrate, arabitol and mannitol).

In other particular embodiments, that additional drug that inhibit cell stress response is selected from the drug or drugs bind to or modulate the activity of a protein encoded by a gene selected from ACCN1, ADRA1A, ADRB2, AFADIN, AKT, ALDH2, ALOX12, AMPK, APBA1, APBA2BP, APG1, APG12, APOER2, ATG5, ATG7, ATM, ATP1A1, ATP2A3, ATP2B1, ATP6V1C1, ATR, BACE1, BAD, BAX, BCAR1, BCL2, BECLIN1, BK channels (KCNMA1, KCNMB1), BRCA1, CACNA1C, CALCINEURIN, CD36, CD44, CDH1, CDH2, CDK5, CDKN1A, CHK1, CHRM1, CHRM2, CHRM3, CHRM4, CHRM5, CK1, CTNNA2, CTNNB1, CULLIN1, CYCLINE, DCC, DGKB, DGKH, DNAJB9, DOCK3, DRD2, EDNRA, ELAVL2, ERK1, ERK2, EZRIN, FAS, FKBP12, FKBP12.6, FOXO3A, FZ2, GADD45, GNPTAB, GPC5, GRK2, GRK5, GRP170, GRIN2B, GRIN3A, GSK3B, HAS1, HAS2, HAS3, HIPK2, HSPA5, HSP90B1, HSPA5, HTR1A, IDE, IMPDH1, IMPDH2, INS, INSR, IRF1, ITB1, ITGA1, ITGB1, ITPR1, JNK1, LAMA1, MAD1L1, MAO, MCC1, MDM1, MME, MOESIN, MTOR, NADPH OXIDASE, NEDD9, NETRIN1, NFKB1, NHERF, NOS1, NOS2A, NOS3, PAELR, PAK1, PARK2, PCAF, PDE11A, PDE3A, PDE4D, PDE5, PDE6D, PI3K, PIK3C3, PKCA, PLCB1, PLD2, PLN, PML, POP2, PRDX5, PRDX6, PRKG1, PTPRG, PTPRM, PVRL1, RAC1, RACK1, RADIXIN, RHOA, ROR2, RTN1, RYR3, SAPK3, SCN1A, SCN1B, SCNN1D, SCNN1G, SH3BP5, SILL SLC8A1, SLC8A2, SLC8A3, SLN, SNCA, SNCAIP, SORBS2, SORCS2, SRC, SYN1, THBS2, TP53, TP63, TRPC3, TRPC4, TRPC5, UNC5C, VPS15, WNT1A, WNT5A, WWOX, XANTHINE OXIDASE, and YES1.

The inventors have established that the above drugs and drug combinations provide improved and synergistic biological effect leading to an effective correction or normalization or functional dysregulation leading to AD and related disorders.

The above named compounds are listed in the following table, together with their CAS number. As discussed before, it should be understood that the invention encompasses the use of the above compounds as well as any pharmaceutically acceptable salt, hydrate, ester, ether, isomers, racemate, conjugates, or pro-drugs thereof. Prodrugs may be prepared (e.g., by coupling the drug to a suitable carrier) to offer a better control over the pharmacokinetic parameters of the treatment.

TABLE 1

| DRUG NAME | CAS NUMBER |
|---|---|
| Acamprosate | 77337-76-9 |
| Albuterol | 18559-94-9 |
| Alendronate | 66376-36-1 |
| Amlodipine | 88150-42-9 |
| Arabitol | 488-82-4, 7643-75-6, 6018-27-5 |
| Cilostazol | 73963-72-1 |
| Dasatinib | 302962-49-8 |
| Fosphenytoin | 93390-81-9 |
| Leflunomide | 75706-12-6 |
| Mannitol | 69-65-8 |
| Metaraminol | 54-49-9 |
| Methimazole | 60-56-0 |
| Milrinone | 78415-72-2 |
| Nitroprusside | 15078-28-1 |
| Omeprazole | 73590-58-6 |
| Phenformin | 114-86-3 |
| Sodium phenylbutyrate | 1716-12-7 |
| Prilocaine | 721-50-6 |
| Rapamycin | 53123-88-9 |
| Rifabutin | 72559-06-9 |
| Sulfisoxazole | 127-69-5 |
| Tadalafil | 171596-29-5 |
| Terbinafine | 91161-71-6 |
| Thioguanine | 154-42-7 |
| Trehalose | 99-20-7 |
| Levosimendan | 141505-33-1 |
| Vidarabine | 24356-66-9 |
| Zonisamide | 68291-97-4 |

Examples of pharmaceutically acceptable salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Additional examples of pharmaceutically acceptable inorganic or organic acid addition salts are listed in e.g., J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Therapy according to the invention may be performed alone or as drug combination, and/or in conjunction with any other therapy, targeting the same pathway or having distinct modes of actions. It and may be provided at home, the doctor's office, a clinic, a hospital's outpatient department, or a hospital, so that the doctor can observe the therapy's effects closely and make any adjustments that are needed.

In a particular embodiment, the compositions of this invention further comprise at least one drug that modulates angiogenesis, preferably that increases angiogenesis, for combined, separate or sequential use. More preferably, the drugs that modulate angiogenesis are selected from the group consisting of ambrisentan, aminocaproic acid, argatroban, balsalazide, becaplermin, cabergoline, clopidogrel, desirudin, dihydroergotamine, eplerenone, fenoldopam, fludrocortisone, gemfibrozil, hesperetin, leflunomide, L-histidine, liothyronine, marimastat, meloxicam, mepacrine, methazolamide, montelukast, netilmicin, nitroglycerin, pyrimethamine, sulfisoxazole, sunitinib, thiethylperazine, tirofiban, topotecan and warfarin (see table 2 below).

TABLE 2

| DRUG NAME | CAS NUMBER |
| --- | --- |
| Ambrisentan | 177036-94-1 |
| Aminocaproic acid | 60-32-2 |
| Argatroban | 74863-84-6 |
| Balsalazide | 80573-04-2 |
| Becaplermin | 165101-51-9 |
| Cabergoline | 81409-90-7 |
| Clopidogrel | 113665-84-2 |
| Desirudin | 120993-53-5 |
| Dihydroergotamine | 6190-39-2 |
| Eplerenone | 107724-20-9 |
| Fenoldopam | 67227-57-0 |
| Fludrocortisone | 127-31-1 |
| Gemfibrozil | 25812-30-0 |
| Hesperetin | 520-33-2 |
| Leflunomide | 75706-12-6 |
| L-histidine | 71-00-1 |
| Liothyronine | 6893-02-3 |
| Marimastat | 154039-60-8 |
| Meloxicam | 71125-38-7 |
| Mepacrine | 83-89-6 |
| Methazolamide | 554-57-4 |
| Montelukast | 158966-92-8 |

TABLE 2-continued

| DRUG NAME | CAS NUMBER |
| --- | --- |
| Netilmicin | 56391-56-1 |
| Nitroglycerin | 55-63-0 |
| Pyrimethamine | 58-14-0 |
| Sulfisoxazole | 127-69-5 |
| Sunitinib | 557795-19-4 |
| Thiethylperazine | 1420-55-9 |
| Tirofiban | 144494-65-5 |
| Topotecan | 119413-54-6 |
| Warfarin | 81-81-2 |

Alternatively, or in addition to the preceding embodiment, the compositions of this invention may further comprise at least one drug that modulates synapse function, preferably that ameliorates synapse function, for combined, separate or sequential use. More preferred drugs that modulate synapse function are selected from alfentanil, amiloride, amlodipine, aztreonam, baclofen, buclizine, bumetanide, buprenorphine, Lidocaine, chlorzoxazone, cinacalcet, dyphylline, eletriptan, ergotamine, flunitrazepam, imatinib, ketotifen, pegaptanib, pentazocine, phenobarbital, pregabalin, propylthiouracil, temazepam, tiagabine, topiramate, triamterene, and vigabatrin (see table 3 below).

TABLE 3

| DRUG NAME | CAS NUMBER |
| --- | --- |
| Alfentanil | 71195-58-9 |
| Amiloride | 2016-88-8 |
| Amlodipine | 88150-42-9 |
| Aztreonam | 78110-38-0 |
| Baclofen | 1134-47-0 |
| Buclizine | 82-95-1 |
| Bumetanide | 28395-03-1 |
| Buprenorphine | 52485-79-7 |
| Chlorzoxazone | 95-25-0 |
| Cinacalcet | 226256-56-0 |
| Dyphylline | 479-18-5 |
| Eletriptan | 143322-58-1 |
| Ergotamine | 113-15-5 |
| Flunitrazepam | 1622-62-4 |
| Imatinib | 152459-95-5 |
| Ketotifen | 34580-14-8 |
| Lidocaine | 137-58-6 |
| Pegaptanib | 222716-86-1 |
| Pentazocine | 359-83-1 |
| Phenobarbital | 50-06-6 |
| Pregabalin | 148553-50-8 |
| Propylthiouracil | 51-52-5 |
| Temazepam | 846-50-4 |
| Tiagabine | 115103-54-3 |
| Topiramate | 97240-79-4 |
| Triamterene | 396-01-0 |
| Vigabatrin | 60643-86-9 |

In a particular embodiment, the invention relates to a composition comprising a drug that inhibits cell stress response, a drug that increases angiogenesis, and a drug that ameliorates synapse function, for simultaneous, separate or sequential administration.

In another particular embodiment, the invention uses a drug that exhibits at least two of the above-listed activities. Indeed, drugs that inhibit cell stress response and that also increase angiogenesis or ameliorate synapse function represent particularly advantageous embodiments of this invention.

Other therapies used in conjunction with drug(s) or drug(s) combination(s) according to the present invention, may comprise one or more drug(s) that ameliorate symptoms of Alzheimer's disease or drug(s) that could be used for palliative treatment of Alzheimer's disease. Preferably, said one or more drug(s) is/are selected from 3APS, AAB-001, ABT-089, ABT-126, AC-3933, ACC-001, Acetaminophen, AFFITOPE AD01, AFFITOPE AD02, alpha-lipoic acid, alpha-tocopherol, AN1792, anti-Abeta, AQW051, Aripiprazole, Atomoxetine, Atorvastatin, AVE1625, AVP-923, AZD0328, AZD3480, Bapineuzumab, BAY94-9172 (ZK 6013443), Bifeprunox, Bioperine, BMS-708163, BRL-049653, Bryostatin, CAD106, Celecoxib, CERE-110, Cerebrolysin, CHF 5074, Choline, Circadin, Citalopram, Coenzyme Q, Copper, CTS21166, Curcumin, CX516 (Ampalex), CX717, Cyclophosphamate, DCB-AD1, Dextroamphetamine, DHA (Docosahexaenoic Acid), Digoxin, Dimebon (Latrepirdine), Divalproex, DMXB-A, Donepezil, Doxycycline, Egb 761, EHT 0202 tazolate, ELND005 (scyllo-inositol), EPAX 1050TG, Ergoloid mesylate, Epigallocatechin-Gallate, Escitalopram, Estradiol, Estrogen, Etanercept, EVP-6124, EVT101, Exelon, Fish oil, FK962, florpiramine F 18, Folate+Vitamin B6+Vitamin B21, Gabapentin, Galantamine, Gemfibrozil, *Ginkgo biloba* extracts (for example EGb 761 or CP401), improved extracts of *Ginkgo biloba* (for example enriched in active ingredients or lessened in contaminant) or drug containing *Ginkgo biloba* extracts (for example Tanakan or Gingkor fort), Glucose, L-Glutamic Acid, GSI 136, GSI-953, GSK239512, GSK933776A, Haloperidol, HF0220, Huperzine A, hydrocodone/APAP, Ibuprofen, IFN-alpha2A, Indomethacin, Insulin, Intravenous Immunoglobulin, Ketasyn, Lecozotan, Leuprolide, Levodopa, Lipoic Acid, Lithium, Lorazepam, Lovostatin, Lutein, LY2062430 (solanezumab), LY2811376, LY450139, LY451395, MABT5102A, Malate, Masitinib (AB1010), Medroxyprogesterone, Melatonin, MEM 1003, MEM 3454, Memantine, Methylene blue, Methylphenidate, Mifepristone, MK0249, MK0677, MK0952, MK0952, MK3328, Modafinil, MPC-7869, NADH, Naproxen, Nefiracetam, Neptune Krill Oil, Neramexane, NICS-15, Nicoderm Patch, Nicotinamide (vitamin B3), Novasoy, NP031112, NS 2330, NSA-789, NSAIDs, Olanzapine, omega-3 polyunsaturated fatty acids (EPA+DHA), ONO-2506PO, Oxybate, *Panax Ginseng*, PAZ-417, PBT2, Perphenazine, PF-04360365, PF-04447943, PF-04494700, Phenserine, Phosphatidylserine, Pitavastatin, Posiphen, PPI-1019 (APAN), Pravastatin, Prazosin, Prednisone, Progesterone, PRX-03140, PYM50028, Quetiapine, R1450, Raloxifene, Ramipril, Rasagiline, Razadyne, resveratrol, rifampicin, risperidone, Rivastigmine, RN1219, R05313534, Rofecoxib, Rosiglitazone, *Salvia officinalis* (sage), SAM-315, SAM-531, SAM-760, SB-742457, Selenium, Sertraline, SGS-742, Simvastatin, SK-PC-B70M, Solanezumab, SR57667B, SRA-333, SRA-444, SSR180711c, ST101, T-817MA, Tacrine, Tarenflurbil, Testosterone, Tramiprosate (3APS), Trazodone, TRx0014 (methylthioninium chloride), Tryptophan, V950, Valproate, Varenicline, Vitamin C, Vitamin E, VP4896, Xaliproden, Zeaxanthin, Zolpidem, and ZT-1 (DEBIO-9902 SR).

The compositions of the invention typically comprise one or several pharmaceutically acceptable carriers or excipients. The duration of the therapy depends on the stage of the disease being treated, the combination used, the age and condition of the patient, and how the patient responds to the treatment.

The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recover from any as yet unforeseen side-effects. The drugs may also be formulated together such that one administration delivers all drugs.

The administration of each drug of the combination may be by any suitable means that results in a concentration of the drug that, combined with the other component, is able to correct the functioning of pathways implicated in AD.

While it is possible for the active ingredients of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained in any appropriate amount in any suitable carrier substance, and is may be present in an amount of 1-99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Several drugs may be mixed together in the tablet, or may be partitioned. For example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The Emulsifying Agents May be Naturally Occurring Gums (e.g., Gum Acacia or Gum Tragacanth)

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

Administration can be one to several times daily for several days to several years, and may even be for the life of the patient. Chronic or at least periodically repeated long-term administration will be indicated in most cases.

Additionally, pharmacogenomic (the effect of genotype on the pharmacokinetic, pharmacodynamic or efficacy profile of a therapeutic) information about a particular patient may affect the dosage used.

Except when responding to especially impairing AD disease cases where higher dosages may be required, the preferred dosage of each drug in the combination usually lies within the range of doses not above those usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually no substantial effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ⅒ to 1/100 of therapeutic doses. At such sub-optimal dosages, the compounds alone would be substantially inactive, while the combination(s) according to the invention are fully effective.

A preferred dosage corresponds to amounts from 1% up to 50% of those usually prescribed for long-term maintenance treatment. Specific dosages correspond to amounts from 1% up to 10% of those usually prescribed for long-term maintenance treatment.

Examples of preferred dosages are given below:
Acamprosate orally from about 1 to 50 mg per day.
Amlodipine orally from about 0.05 to 5 mg per day.
Cilostazol orally from about 1 to 50 mg per day.
Leflunomide orally from about 0.25 to 12.5 mg per day.
Methimazole orally from about 0.05 to 30 mg per day.
Phenformin orally from about 0.5 to 25 mg per day.
Sulfisoxazole orally from 0.4 to 4 g per day divided in 4 to 6 doses.
Tadalafil orally from about 0.05 to 2.5 mg per day.
Terbinafine orally from about 2.5 to 75 mg per day.
Zonisamide orally from about 1 to 200 mg per day.
Rifabutin orally from about 3 to 300 mg per day.

Examples of dosages in combined therapies are provided below:
  phenformin orally from about 0.5 to 5 mg per day and rifabutin orally from about 6 to 60 mg per day
  phenformin orally from about 0.5 to 5 mg per day and arabitol orally from about 50 to 500 mg per day.
  tadalafil orally from about 0.05 to 0.5 mg per day and omeprazole orally from about 0.4 to 4 mg per day.
  cilostazol orally from about 1 to 10 mg per day and omeprazole orally from about 0.4 to 4 mg per day.
  phenformin orally from about 0.5 to 5 mg per day and dasatinib orally from about 1 to 10 mg per day
  dasatinib orally from about 1 to 10 mg per day and acamprosate orally from about 7 to 70 mg three times daily
  dasatinib orally from about 1 to 10 mg per day and terbinafine orally from about 2.5 to 25 mg once or twice daily It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

I. The Compounds Prevent Toxicity of $A\beta_{25-35}$ Peptide

In this first series of experiments, candidate compounds have been tested for their ability to prevent or reduce the toxic effects of $A\beta_{25-35}$ peptide.

The regulation of APP expression represents an important entry point for AD treatment since it is situated upstream of generation of particular toxic fragments and their action on multiple brain systems eventually resulting in destruction of cognitive functions.

In AD, the protein forms aggregates of insoluble β-pleated sheets of fibrillar Abeta protein (amyloid). The conformational change from soluble to fibrillar forms seems to be a spontaneous event that is increased with higher concentrations of Abeta, so any production of larger amounts of Abeta than normal (or production of the larger, less soluble forms of Abeta) will tend to increase plaque formation. Once the Abeta plaque has started to form, other molecules can interact with the nascent plaque to produce eventually the mature plaque with its associated areas of neuronal cell death. Considering this, we have evaluated the effects of the compounds on the viability of the cells exposed to the amyloid 13 protein.

PC12 Cell Culture

PC12 (Pheochromocytoma Rat, ATCC ref: CRL-1721) cells from ATCC (ATCC CRL-1721) were rapidly thawed in 37° C. water. The supernatant was immediately put in 9 ml of a "PC12 proliferation medium" containing Dulbecco's modified Eagle's medium DMEM-F12 (Pan Biotech ref: P04-41450) with 15% heat-inactivated horse serum (Invitrogen ref: 16050-130), 2.5% of fetal bovine serum (FBS; Invitrogen ref: 16000-036), 1% of Penicillin 10.000 U/ml and Streptomycin 10 mg/ml (PS; Pan Biotech ref: P06-07100) and 1% de L-glutamine 200 mM (Pan Biotech Ref: P04-80100).

Cells were centrifuged (800 rounds/min, 4° C. for 5 min) and added in 5 ml "PC12 proliferation medium", viable cells were counted with a Malassez cell using the neutral red exclusion test (Sigma).

Then the cells were seeded at $3 \cdot 10^4$ cells per $cm^2$ in "PC12 proliferation medium" in 75 $cm^2$ plastic flasks (Greiner Ref: 658175) precoated with poly-L-lysine (10 μg/ml, Sigma Ref: P2636).

Medium was changed every other day. After 3 days of culture, when cells reached 80% of confluence, they were washed in HBSS without calcium and magnesium (Pan Biotech Ref: P06-33500) and incubated in trypsin EDTA, (0.05%, Pan Biotech Ref: P10-023100). The enzymatic reaction was stopped with PC12 proliferation medium added by 0.5 mg/ml of DNAse 1 grade 2 (Pan Biotech Ref: T60-37780100). Then, PC12 were centrifuged (800 rounds/min at 4° C. for 10 min) and cells were seeded at the density of 2.9 $10^4$ per $cm^2$ in 175 $cm^2$ culture flask (Greiner Ref: 661195) pre-coated with poly-L-lysine.

Intoxication and MTT Viability Assay:

PC12 cells (passage #2) are seeded on the basis of 3300 cells per $cm^2$ in 96 well-plates (Greiner Ref: 655 180) pre-coated with poly-L-lysine (Sigma) Neurobasal medium (Invitrogen, Ref: 21103049) containing B27 (2%, Invitrogen, Ref: 21103049), penicillin (50 U/ml)-streptomycin (50 μg/ml) and glutamine (1%) and 50 ng/ml of NGF (Sigma Ref: N1408). NGF allow PC12 to differentiate in sympatic neuron-like cells.

After 5 days of culture, the medium is changed with neurobasal added by NGF (50 ng/ml), B27 without antioxidant, glutamine and antibiotics. After 24 h, cells are incubated for 1 hour with drugs at 5 concentrations, 6 wells per conditions. After 1 hour of pre-incubation, cells are intoxicated by 10 μM of beta-amyloid (25-35; Sigma) together with drugs in the cell culture medium. 24 h later, cells are washed once with PBS (Pan Biotech, Ref: P04-36100) and the PC12 cell survival was evaluated by MTT (3,[4,5-dimethylthiazol-2-yl]-2,5 diphenyltetrazoliumbromide) viability test.

Cortical Neurons Cell Culture

Primary rat cortical neurons are cultured as described by Singer et al., 1999. Briefly pregnant female rats of 15 days gestation are killed by cervical dislocation (Rats Wistar; Janvier) and the foetuses removed from the uterus. The cortex are removed and placed in ice-cold medium of Leibovitz (L15; Invitrogen) containing 1% of Penicillin-Streptomycin (PS; Invitrogen) and 1% of bovine serum albumin (BSA; Sigma). Cortex are dissociated by trypsinisation for 20 min at 37° C. (Trypsin EDTA 1×; Invitrogen) diluted in PBS without calcium and magnesium. The reaction is stopped by the addition of Dulbecco's modified Eagle's medium (DMEM; Invitrogen) containing DNAase I grade II (0.1 mg/ml; Roche Diagnostic) and 10% of foetal calf serum (FCS; Invitrogen). Cells are then mechanically dissociated by 3 passages through a 10 ml pipette. Cells are then centrifuged at 180×g for 10 min at 10° C. The supernatant is discarded and the cells of pellet are re-suspended in a defined culture medium consisting of Neurobasal (Invitrogen) supplemented with B27 (2%; Invitrogen), L-glutamine (0.2 mM; Invitrogen), 1% of PS solution and 10 ng/ml of Brain-derived neurotrophic factor (BDNF, Pan Biotech). Viable cells are counted in a Neubauer cytometer using the trypan blue exclusion test. Cells are seeded at a density of 30 000 cells/well in 96 well-plates (wells are precoated with poly-L-lysine (10 ng/ml; Sigma)) and are cultured at 37° C. in a humidified air (95%)/CO2 (5%) atmosphere.

After 6 days of culture, cells are incubated with drugs (5 concentrations). After 1 hour, cells are intoxicated by 20 µM of β-amyloid (25-35; Sigma) in defined medium without BDNF but together with drugs. Cortical neurons are intoxicated for 2 days. BDNF (10 ng/ml) is used as a positive (neuroprotective) control.

Lactate Dehydrogenase (LDH) Activity Assay.

After 2 days of culture, the supernatant is collected and analyzed with Cytotoxicity Detection Kit (LDH, Roche Applied Sciences). This colorimetric assay for the quantification of cell death is based on the measurement of lactate dehydrogenase (LDH) activity released from the cytosol of damaged cells into the supernatant. The optic density (DO) is assessed by spectrophotometer at 492 nm wavelength by a multiscan apparatus (Thermo, Ref Ascent). Results are expressed in percentage of cell viability, compared to the negative control (vehicle).

Results

Figure 2:
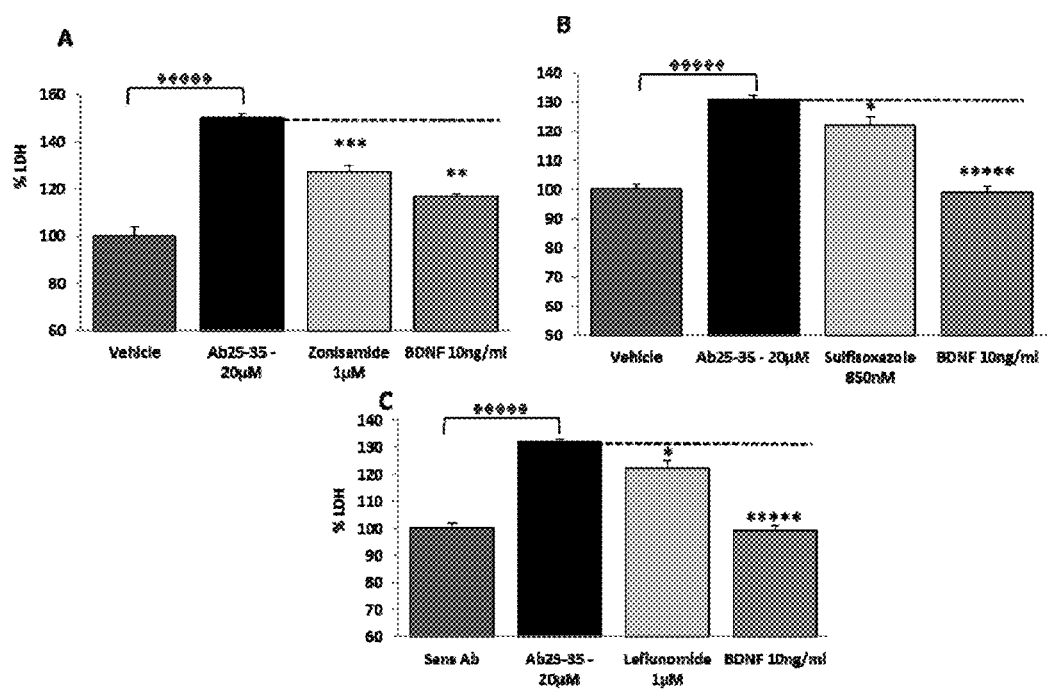
FIG. 2: Effect of selected drugs on LDH release in beta-amyloid intoxicated rat primary cortical neuron culture. ◊◊◊◊◊: $p<0.000001$: significantly different from vehicle. *:$p<0.05$;:$p<0.01$; *:$p<0.001$ *****:$p<0.00001$: significantly different from A$\beta_{25-35}$. Bilateral Student's t test. A$\beta_{25-35}$ 20 µM produces a significant intoxication, above 25%, compared to vehicle-treated neurons (FIGS. 2-A, B and C). This intoxication is efficiently prevented by BDNF at 10 ng/ml, which is considered as a positive control for neuroprotection. This intoxication is also significantly prevented by either Zonisamide (FIG. 2A), Sulfisoxazole (FIG. 2B) or Leflunomide (FIG. 2C).

Results presented in FIGS. 1 and 2 are extracted from two independent cultures, 6 wells per condition. All values are expressed as mean±s.e.mean. A bilateral Student's t test analysis is performed on raw data. Results are expressed in percentage of neurites length, compared to the control (vehicle).

NGF-differentiated PC12 cells are incubated with drugs one hour before Abeta$_{25-35}$ 10 µM intoxication that lasts 24 hours. One day after this incubation, the viability of NGF-differentiated PC12 is quantified, using MTT assay. The results presented FIG. 1 clearly demonstrate a neuroprotective effect of the tested drugs of the invention against Abeta$_{25-35}$ intoxication.

Rat primary cortical neurons are incubated with drugs one hour before Aβ$_{25-35}$ 20 µM intoxication that lasts 2 days. Two days after this incubation, LDH release in the culture medium is quantified, reflecting the level of cell death. The results show that the tested drugs clearly exert a protective effect against this Aβ$_{25-35}$ intoxication (FIG. 2).

II. Compounds and Combinations Thereof Prevent Toxicity of Human Aβ$_{1-42}$ Peptide In this further series of experiments, candidate compounds have been tested for their ability to prevent or reduce the toxic effects of human Aβ$_{1-42}$. Aβ$_{1-42}$ is the full length peptide that constitutes aggregates found in biopsies from human patients afflicted with AD. The drugs are first tested individually, followed by assays of their combinatorial action. The effect is determined on various cell types, to further document the activity of the compounds.

II.1. Protection Against the Toxicity of Human Aβ$_{1-42}$ Peptide in Rat Primary Cortical Neuron Cells Test Compound and Human Amyloid-β1-42 Treatment Primary rat cortical neurons are cultured as described previously.

Briefly, Aβ$_{1-42}$ peptide was reconstituted in define culture medium at 40 µM (mother solution) and was slowly shaked at +37° C. for 3 days in dark. The control medium was prepared in the same conditions.

After 3 days, the solution was used on primary cortical neurons as follows:

After 10 days of neuron culture, drug was solved in culture medium (+0.1% DMSO) and then pre-incubated with neurons for 1 hour before the Aβ$_{1-42}$ application (in a final volume per culture well of 100 µl). One hour after drug incubation, 100 µl of Aβ$_{1-42}$ peptide was added to a final concentration of 10 µM diluted in presence of drug, in order to avoid further drug dilutions. Cortical neurons were intoxicated for 24 hours. Three separate cultures were performed per condition, 6 wells per condition.

BDNF (50 ng/ml) and Estradiol-β (100 and 150 nM) were used as positive control and reference compounds respectively. Three separate cultures will be performed per condition, 12 wells per condition.

Organization of Culture Plates

Estradiol-β at 100 and 150 nM were used as reference test compound and BDNF at 50 ng/ml was used as a positive control.

Estradiol-β and BDNF were solved in culture medium and pre-incubated for 1 h before the amyloid-β$_{1-42}$ application.

The following conditions were assessed:
1 CONTROL PLAQUE: 12 wells/condition
  Negative Control: medium alone+0.1% DMSO
  Intoxication: amyloid-β$_{1-42}$ (10 µM) for 24 h
  Positive control: BDNF (50 ng/ml) 1 hr followed by amyloid-β$_{1-42}$ (10 µM) for 24 h
  Reference compound: Estradiol (150 nM) 1 hr followed by amyloid-β$_{1-42}$ (10 µM) for 24 h.
DRUG PLATE: 6 wells/condition
  Negative Control: medium alone+0.1% DMSO
  Intoxication: amyloid-β$_{1-42}$ (10 µM) for 24 h
  Drug 1: Drug 1-1 hr followed by amyloid-β$_{1-42}$ (10 µM) for 24 h
  Drug 2: Drug 2-1 hr followed by amyloid-β$_{1-42}$ (10 µM) for 24 h Lactate Dehydrogenase (LDH) Activity Assay 24 hours after intoxication, the supernatant was taken off and analyzed with Cytotoxicity Detection Kit (LDH, Roche Applied Science, ref: 11644793001, batch: 11800300). This colorimetric assay for the quantification of cell toxicity is based on the measurement of lactate dehydrogenase (LDH) activity released from the cytosol of dying cells into the supernatant.

Data Processing

All values are expressed as mean±s.e.mean of the 3 cultures (n=6 per condition). Statistic analyses were done on the different conditions (ANOVA followed by the Dunnett's test when it was allowed, Statview software version 5.0).

Results

Figure 4:
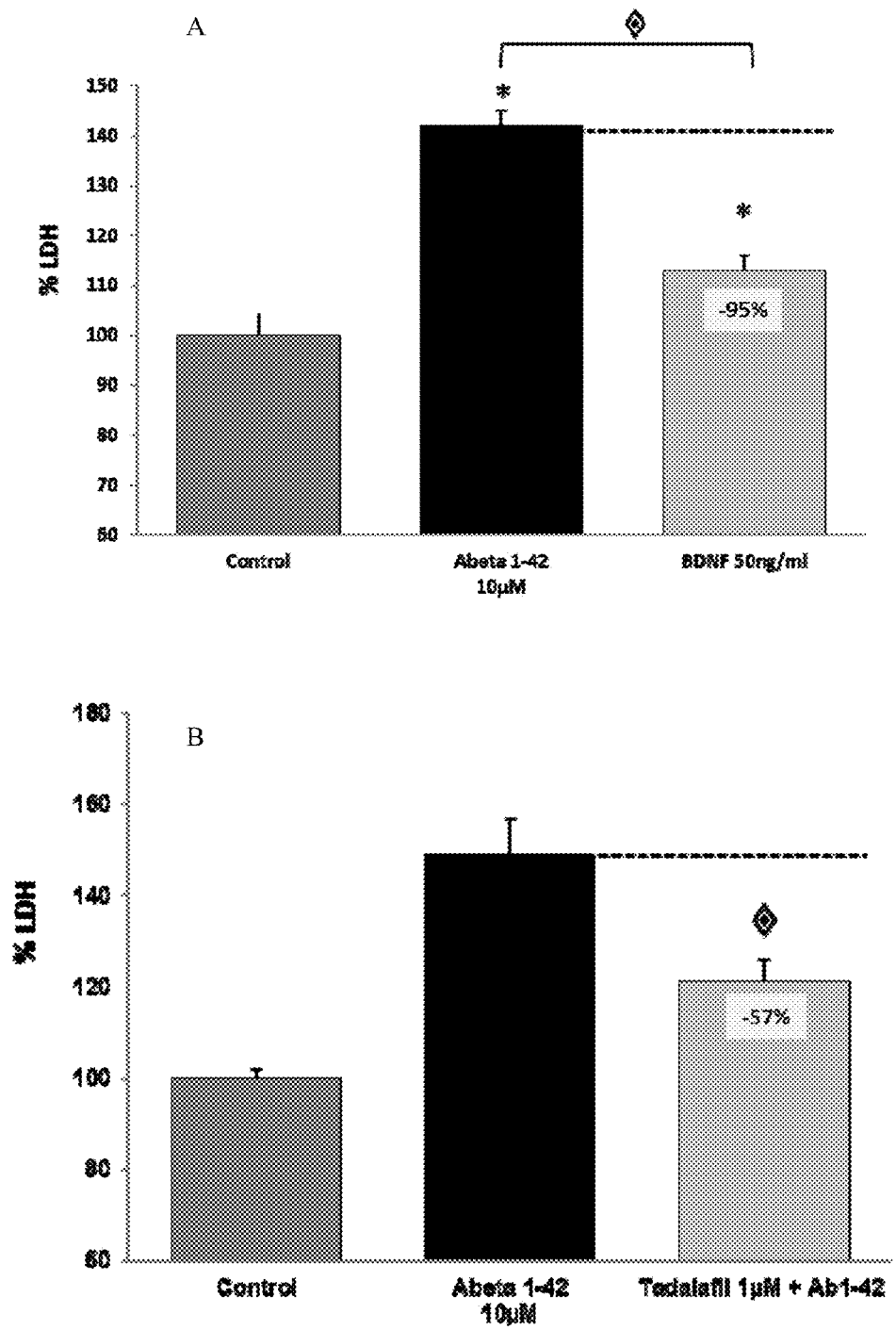
FIG. 4: Effect of Tadalafil on LDH release in human A$\beta_{1-42}$ intoxicated rat primary cortical neuron culture. A$\beta_{1-42}$ produces a significant intoxication compared to vehicle-treated neurons. A) 1 hr of BDNF pre-treatment significantly protected the neurons from this amyloid injury (−95%). *: $p<0.05$: significantly different from control (no intoxication) ◊ : $p<0.05$: significantly different from Amyloid intoxication (ANOVA+Dunett Post-Hoc test). B) The intoxication is significantly prevented by Tadalafil (−57% of LDH release compared to amyloid intoxication). ◊ : $p<0.05$: significantly different from Amyloid intoxication (ANOVA+Dunett Post-Hoc test).

The results are presented in FIG. 4 and in table 4 below.

TABLE 4

| DRUG NAME | Protective effect on Aβ$_{1-42}$ toxicity in neuronal cells |
|---|---|
| Baclofen (+/−) | + |
| Leflunomide | + |
| Phenformin | + |
| Sulfisoxazole | + |
| Tadalafil | + |
| Zonisamide | + |

These results clearly demonstrate a substantive effect of the drugs of the invention on Aβ$_{1-42}$-intoxicated neural cells. A particularly pronounced effect was observed with Tadafil (FIG. 4) and Sulfisoxazole.

II.2. Protection Against the Toxicity of Human Aβ$_{1-42}$ Peptide on Human Brain Microvascular Endothelial Cells Ultrastructural studies have shown that brain microvessels are closely associated with β-amyloid plaques, and that Alzheimer's disease brain capillaries contain preamyloid deposits (52). Damage to the vasculature resulting from Abeta deposition can result in a reduction of cerebral blood flow (53). Moreover, Abeta peptides have been shown to be potent inhibitors of angiogenesis in vitro and in vivo (54). Aβ1-42 is the full length peptide that constitutes aggregates found in biopsies from human patients that suffered from AD. To be the closest as possible of the human disease, the protection afforded by candidate compounds towards Aβ1-42 was assessed.

We chose to use Human Brain Microvascular Endothelial Cells (HBMEC). This model has been previously used to study the anti-angiogenic properties of mutant forms of Abeta peptide.

Human brain microvascular endothelial cerebral cells (HBMEC, ScienCell Ref: 1000, frozen at passage 10) were rapidly thawed in a waterbath at +37° C. The supernatant was immediately put in 9 ml Dulbecco's modified Eagle's medium (DMEM; Pan Biotech ref: P04-03600) containing 10% of foetal calf serum (FCS; GIBCO ref 10270-106). Cell suspension was centrifuged at 180×g for 10 min at +4° C. and the pellets were suspended in CSC serum-free medium (CSC serum free, Cell System, Ref: SF-4Z0-500-R, Batch 51407-4) with 1.6% of Serum free RocketFuel (Cell System, Ref: SF-4Z0-500-R, Batch 54102), 2% of Penicillin 10.000 U/ml and Streptomycin 10 mg/ml (PS; Pan Biotech ref: P06-07100 batch 133080808) and were seeded at the density of 20 000 cells per well in 96 well-plates (matrigel layer biocoat angiogenesis system, BD, Ref 354150, Batch A8662) in a final volume of 100 μl. On matrigel support, endothelial cerebral cells spontaneously started the process of capillary network morphogenesis (54).

Three separate cultures were performed per condition, 6 wells per condition.

Candidate Compounds and Human Amyloid-β$_{1-42}$ Treatment

Briefly, Aβ$_{1-42}$ peptide (Bachem, ref: H1368 batch 1010533) was reconstituted in define culture medium at 20 μM (mother solution) and was slowly shacked at +37° C. for 3 days in. The control medium was prepared in the same conditions.

After 3 days, this human amyloid peptide was used on HBMEC at 2.5 μM diluted in control medium (optimal incubation time). The Aβ$_{1-42}$ peptide was added 2 hours after HBMEC seeding on matrigel for 18 hours incubation.

One hour after HBMEC seeding on matrigel, test compounds and VEGF-165 were solved in culture medium (+0.1% DMSO) and then pre-incubated with HBMEC for 1 hour before the Aβ$_{1-42}$ application (in a final volume per culture well of 100 μl). One hour after test compounds or VEGF incubation (two hours after cell seeding on matrigel), 100 μl of Aβ$_{1-42}$ peptide was added to a final concentration of 2.5 μM diluted in control medium in presence of test compounds or VEGF (in a 200 μl total volume/well), in order to avoid further drug dilutions.

Organization of Culture Plates

VEGF-165, known to be a pro-angiogenic isoform of VEGF-A, was used for all experiments in this study as reference compound. VEGF-165 is one of the most abundant VEGF isoforms involved in angiogenesis. VEGF was used as reference test compound at 10 nM.

The following conditions were assessed:

Negative Control: medium alone+0.1% DMSO

Intoxication: amyloid-β$_{1-42}$ (2.5 μM) for 18 h

Positive control: VEGF-165 (10 nM) (1 reference compound/culture) 1 hr before the Aβ$_{1-42}$ (2.5 μM) addition for a 18 h incubation time.

Test compounds: Test compound I hr before the Aβ$_{1-42}$ (2.5 μM) addition for a 18 h incubation time.

Capillary Network Quantification

Per well, 2 pictures with 4× lens were taken using InCell Analyzer™ 1000 (GE Healthcare) in light transmission. All images were taken in the same conditions. Analysis of the angiogenesis networks was done using Developer software (GE Healthcare). The total length of capillary network was assessed.

Data Processing

All values are expressed as mean±s.e.mean of the 3 cultures (n=6 per condition). Statistic analyses were done on the different conditions performing an ANOVA followed by the Dunnett's test when it was allowed (Statview software version 5.0). The values (as %) inserted on the graphs show the amyloid toxicity evolution. Indeed, the amyloid toxicity was taken as the 100% and the test compound effect was calculated as a % of this amyloid toxicity.

Results

Figure 3:
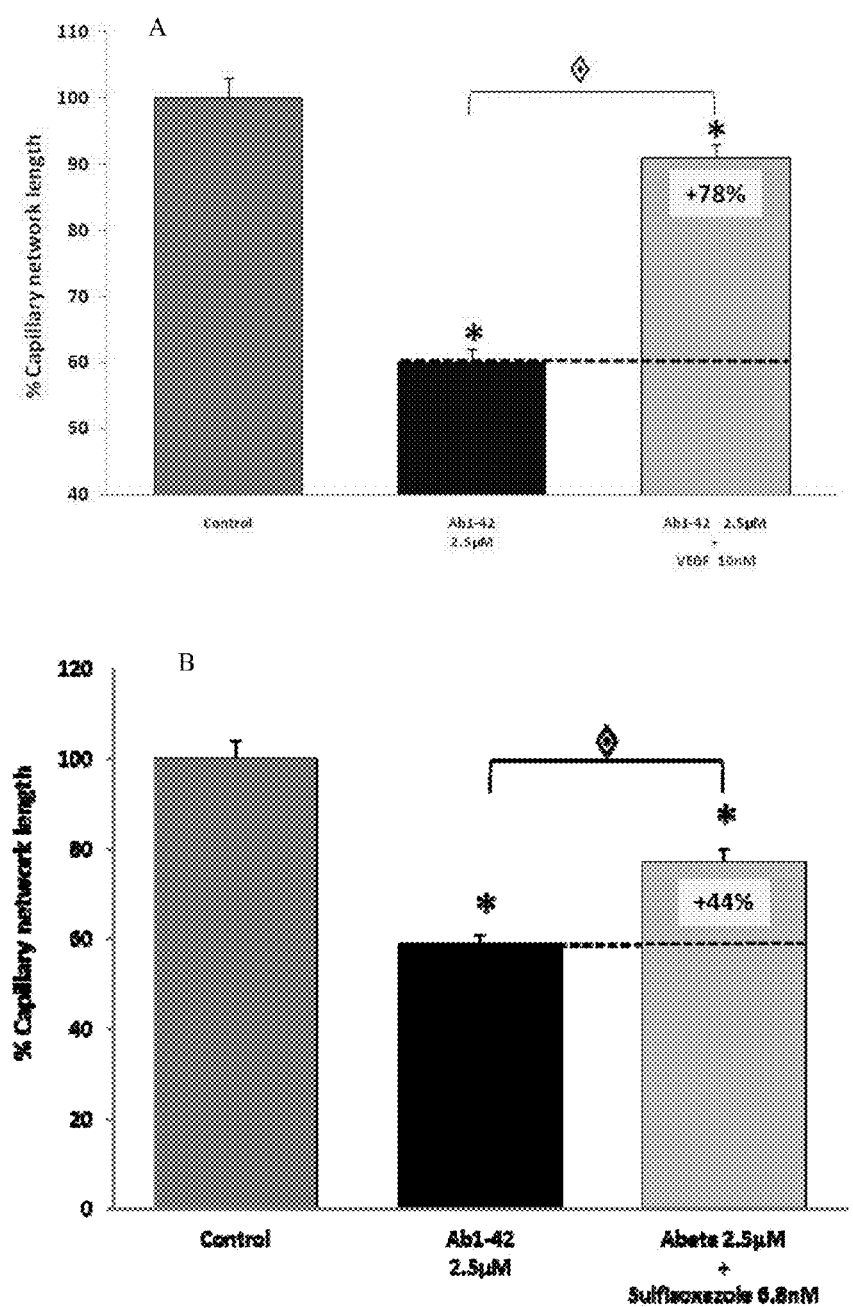
FIG. 3: Effect of sulfisoxazole pretreatment against human A$\beta_{1-42}$ injury in HBMEC. A) 1 hr of VEGF pre-treatment at 10 nM significantly protected the capillary network from this amyloid injury (+78% of capillary network compared to amyloid intoxication). *: $p<0.05$: significantly different from control (no intoxication); ◊ : $p<0.05$: significantly different from Amyloid intoxication (ANOVA+Dunett Post-Hoc test). B) The intoxication is significantly prevented by Sulfisoxazole. ◊ : $p<0.05$: significantly different from Amyloid intoxication (ANOVA+Dunett Post-Hoc test).

The results are shown in FIG. 3 for Sulfisoxazole or in Table 5.

TABLE 5

| DRUG NAME | Protective effect in Aβ$_{1-42}$ intoxicated HBMC |
|---|---|
| Baclofen (+/−) | + |
| Sulfisoxazole | + |
| Terbinafine | + |

These results clearly show a substantial protective effect of single drugs on human cells. A particularly pronounced effect was observed with Sulfisoxazole, as shown in FIG. 3.

II.3 Effect of Combined Therapies on the Toxicity of Human Aβ$_{1-42}$ Peptide on Human HBMEC Cells and on Rat Primary Cortical Neuron Cells The efficacy of drug combinations of the invention was demonstrated on human and rat cells. The protocols used in these assays are the same as described in sections II.1 and II.2 above.

Results

The following drug combinations are tested on human brain microvascular endothelial cells and on rat primary cortical neuron cells:
- sulfisoxazole and zonisamide,
- sulfisoxazole and terbinafine, or
- sulfisoxazole and levosimendan.

All of the tested drug combinations give protective effect against toxicity of human $A\beta_{1-42}$ peptide in both models, as shown in Table 6 below.

TABLE 6

| DRUG NAME | Protective effect on $A\beta_{1-42}$ toxicity in neuronal cells | Protective effect in $A\beta_{1-42}$ intoxicated HBMEC cells |
|---|---|---|
| sulfisoxazole and zonisamide | + | + |
| sulfisoxazole and terbinafine | + | + |
| sulfisoxazole and levosimendan | + | + |

III. Terbinafine and Sulfisoxazole Combination Therapy Effectively Protects Neurons Against Toxicity of Human $A\beta_{1-42}$ In this example, combination therapy using Terbinafine and Sulfisoxazole was assessed for its ability to prevent or reduce the toxic effects of human $A\beta_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 5:
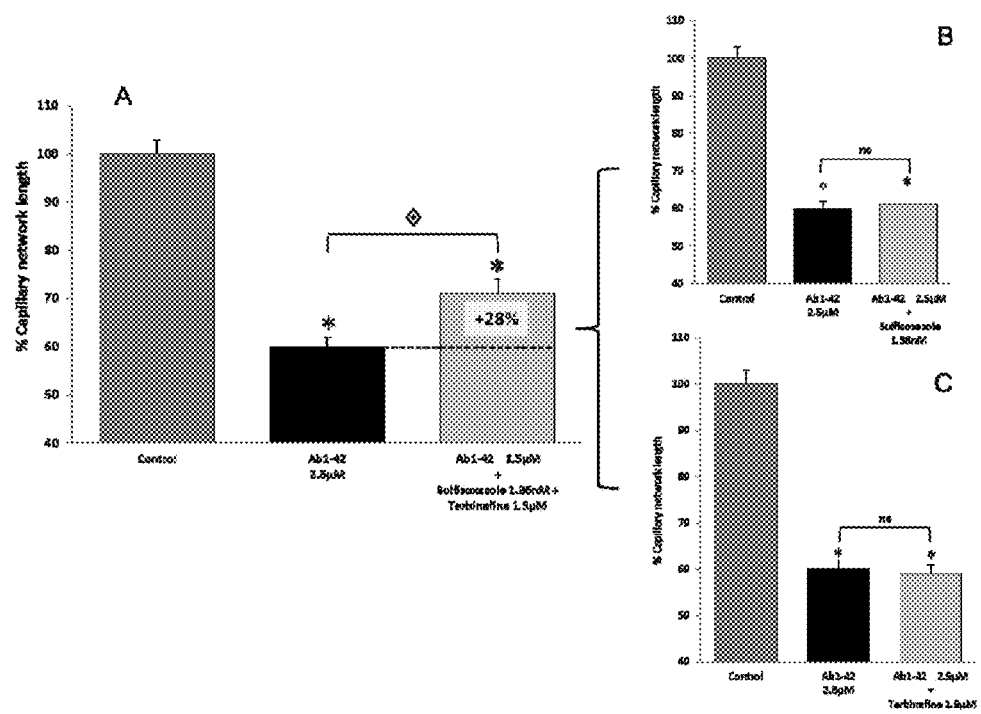
FIG. 5: Effect of a selected combination therapy on the total length of capillary network in beta-amyloid intoxicated HBMEC cultures. ◊ : $p<0.05$: significantly different from A$\beta_{1-42}$. *: $p<0.05$: significantly different from vehicle. ANOVA+Bunett Post-Hoc test. The human amyloid peptide (A$\beta_{1-42}$ 2.5 µM) produces a significant intoxication, above 40%, compared to vehicle-treated neurons. This intoxication is significantly prevented by the combination of Sulfisoxazole and Terbinafine (FIG. 5A) whereas, at these concentrations, Sulfisoxazole and Terbinafine alone have no significant effect on intoxication (FIGS. 5B and 5C).

The results are presented FIG. 5. They clearly show that the aggregated human amyloid peptide ($A\beta_{1-42}$ 2.5 µM) produces a significant intoxication, above 40%, compared to vehicle-treated neurons. This intoxication is significantly prevented by the combination of Terbinafine and Sulfisoxazole (FIG. 5A) whereas, at those concentrations, Sulfisoxazole (FIG. 5B) and Terbinafine (FIG. 5C) alone have no significant effect on intoxication.

IV. Sulfisoxazole and Levosimendan Combination Therapy Effectively Protects Neurons Against Toxicity of Human $A\beta_{1-42}$ In this example, combination therapy using Sulfisoxazole and Levosimendan was assessed for its ability to prevent or reduce the toxic effects of human $A\beta_{1-42}$.

The combination therapy was tested under experimental conditions disclosed in Example II.1. Human brain microvascular endothelial cell cultures were used, as disclosed in II.1., and incubated simultaneously or sequentially with the drug combination.

Figure 6:
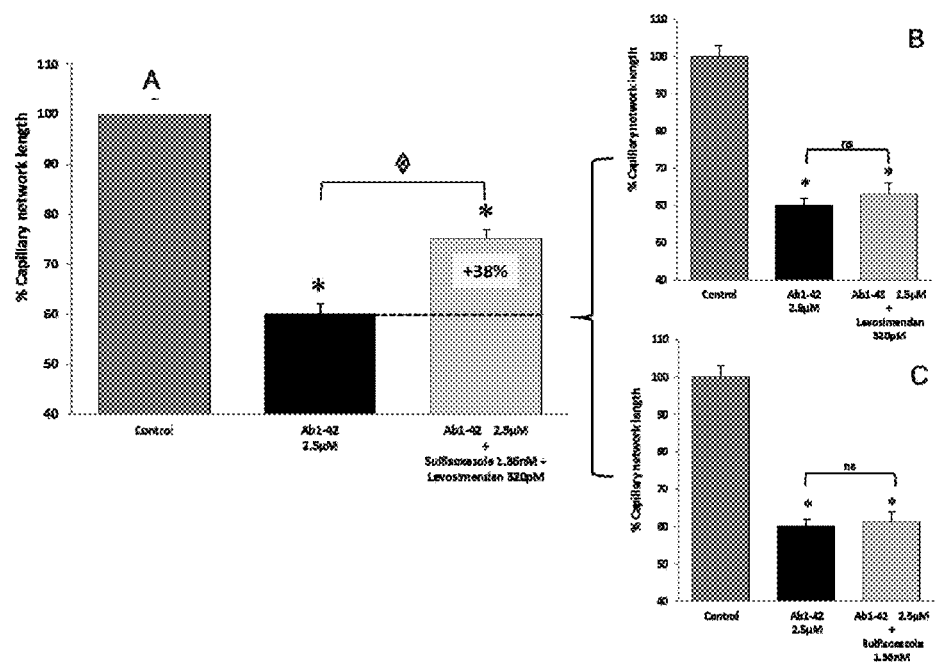
FIG. 6: Effect of a selected combination therapy on the total length of capillary network in beta-amyloid intoxicated HBMEC cultures. ◊ : $p<0.05$: significantly different from A$\beta_{1-42}$. *: $p<0.05$: significantly different from vehicle. ANOVA+Bunett Post-Hoc test. The human amyloid peptide (A$\beta_{1-42}$ 2.5 µM) produces a significant intoxication, above 40%, compared to vehicle-treated neurons. This intoxication is significantly prevented by the combination of Sulfisoxazole and Levosimendan (FIG. 6A) whereas, at these concentrations, Sulfisoxazole and Levosimendan alone have no significant effect on intoxication (FIGS. 6B and 6C).

The results are presented FIG. 6. They clearly show that the aggregated human amyloid peptide ($A\beta_{1-42}$ 2.5 µM) produces a significant intoxication, above 40%, compared to vehicle-treated neurons. This intoxication is significantly prevented by the combination of Sulfisoxazole and Levosimendan (FIG. 6A) whereas, at those concentrations, Levosimendan (FIG. 6B) and Sulfisoxazole (FIG. 6C) alone have no significant effect on intoxication.

V. In Vivo Activity

Compounds and their combinations are tested in an in vivo model of Alzheimer disease. Overexpression of Alzheimer's disease-linked mutant human amyloid beta protein precursor (APP) transgenes has been the most reliable means of promoting deposition of Abeta in the brains of transgenic mice that served as AD disease models in numerous studies. As they age, these mutant APP mice develop robust amyloid pathology and other AD-like features, including decreased synaptic density, reactive gliosis, and some cognitive deficits. Many mutant APP mouse models show little evidence of overt neuronal loss and neurofibrillary tangle (NFT) pathology. Mice hemizygous for this BRI-Abeta42 transgene are viable and fertile with a normal lifespan. Transgenic BRI-Abeta42 mRNA is expressed in a pattern characteristic of the mouse prion protein promoter; highest transgene expression levels are detected in the cerebellar granule cells and hippocampus, followed by the cortex, pons, thalamus, and midbrain. In the transgenic fusion protein, Abeta1-42 is fused to the C terminus of the BRI protein at the furin-like cleavage site such that cleavage results in efficient Abeta1-42 secretion into the lumen or extracellular space. Therefore, these mice specifically express the Abeta1-42 isoform. Hemizygous BRI-Abeta42 mice accumulate detergent-insoluble amyloid-beta with age and develop cored plaques in the cerebellum at as early as 3 months of age. Development of forebrain pathology occurs later, extracellular Abeta plaques are not present consistently in the hippocampus and entorhinal/piriform cortices until 12 months of age. Amyloid beta deposits (cored plaques) can be observed as early as 3 months in molecular layer of cerebella of transgenic mice and becoming more pronounced with age; occasional extracellular plaques are seen in the entorhinal/piriform cortices and hippocampus at 6 months of age, but aren't consistently found until >12 months of age. Oldest mice show widespread pathology with cored and diffuse plaques in cerebellum, cortex, hippocampus, and olfactory bulb. Extracellular amyloid plaques show dense amyloid cores with radiating fibrils; many bundles of dystrophic neurites are observed at the periphery of these plaques. Reactive gliosis is associated with plaques.

Drug Treatments.

The transgenic Tg (Prnp-ITM2B/APP695*42) A12E mc mice (43) has been obtained from Jackson Laboratory (http://jaxmice.jax.org/strain/007002.html). Mice founder with the highest Abeta42 plasma levels, line BRI-Abeta42A (12e), have been maintained on a mixed B6C3 background. Adult male transgenic mice have free access to food and water. In accord with an approved the Institutional Animal Care and Use Committee protocol, mice have been weighed and injected i.p. or force fed once daily for 10 to 20 consecutive weeks with either a control solution (placebo) or PXT drugs, prepared at different doses.

Survival Analysis

Survival rates have been analyzed using Kaplan-Meier methods. Holm-Sidak methods (post hoc) have been used for all pairwise multiple comparison tests. The extraneous deaths are censored. All comparisons have been made between littermates to limit any potentially confounding effects from background strain differences.

Behavioural Tests

Behavioural tests were designed and conducted according to the methods published by several authors (44-47).

Spatial Learning and Memory in the Morris Water Maze (MWM)

This experiment is performed in a circular pool, 90 cm in diameter, made of white plastic and filled with milky colored water. An escape platform, 8 cm in diameter, made of clear plastic was submerged 0.5 cm under the water level. Visual clues are provided by different geometrical forms printed in A4-sized letters and placed on the four surrounding walls (distance from the pool was from 50 to 70 cm). Each mouse has been given four trials daily (5- to 7-minute interval between trials, a total of 16 trials) for 4 days. Each trial has been performed from one of four different starting points. The movement of the mice is monitored using Videotrack Software (View Point). The time taken to locate the escape platform (escape latency; up to 60 seconds) has been determined. After locating the platform the mouse has been allowed to sit on it for 15 seconds. Mice who failed to find the platform within 60 seconds have been guided to it and allowed to stay on it for 15 seconds. A latency of 60 seconds is entered into the record for such an occurrence. All four trials per day have been averaged for statistical analysis, except for the first trial on day 1. On day 9 (5 days after the last training) mice have been subjected to a 60-second probe trial in which the platform is removed and the mice are allowed to search for it. The time that each animal spent in each quadrant has been recorded (quadrant search time). Several groups of male mice have been used at 3, 7, 10, and 12 months.

The some few mice have showed freezing behaviour (eg, lying motionless in the water and refusing to swim) that strongly interfered with the test, these animals have been excluded from the data analysis.

All behavioural tests are conducted under a quiet and light-reduced environment.

Working Memory Test in Radial Arm Water Maze

This cognitive-based sensitive measure of working memory has been obtained with the help of the apparatus consisted of a 100 cm-diameter waterfilled pool (also used for the Morris water maze and Platform Recognition tasks) fitted with an aluminium insert to create six radially-distributed swim arms. Testing consists of five, 1-min trials per daily session, for 9-12 consecutive days. At the start of each session, a clear submerged platform is positioned at the end of one of the six swim arms (randomly-selected, changed daily). For each of the first four acquisition trials, the animal is placed into one of the non-platform containing arms (randomized sequence) and allowed to search for the platform. During the 60 s trial, each time the animal enters another non-platform containing arm, it is gently returned to its starting location and an error recorded. After the fourth trial, the animal is allowed to rest for 30 min, followed by a fifth (retention) trial, which originates in the final non-platform containing swim arm. The number of errors (incorrect arm choices) and escape latency (time to reach platform, maximum 60 s) are recorded for each trial.

Spatial Reference Learning and Memory in Circular Platform Test

This cognitive-based task test is performed with the help of the apparatus that consists of a 69 cm-diameter circular platform having 16 "escape" holes spaced equidistantly around the circumference. An escape refuge is installed beneath one of the holes, and a black curtain, on which are placed various visual cues, encircles the platform. The animal is placed in the center of the platform at the start of a single, 5 min trial and aversive stimuli (bright lights, fan wind) are presented. The total number of errors (head-pokes into non-escape holes) and escape latency (time to reach escape hole) are recorded.

Recognition Ability in Platform Recognition Test

This cognitive-based search task evaluates object identification and recognition ability. The target object consists of a 9 cm-diameter circular platform fitted with a 10 cm×40 cm black ensign, which is positioned 0.8 cm above the surface of the water in a 100 cm-diameter circular pool. Testing consists of four 60 s trials per day on each of four consecutive days. On each day, the target object is placed into a different quadrant of the pool for each trial, and the animal is released at the same location along the circumference of the pool for all four trials. The total latency (maximum 60 s) is recorded for each trial.

Modified Irwin Examination

A comprehensive screen, modified from Irwin is used to determine whether any of the mice exhibited physiological, behavioural, or sensorimotor impairments related to their genotype. To explore motor skills, coordination, and muscle strength, the mice are placed on a wire that was tightened between two 30-cm-high columns and their ability to balance on the wire is assessed. In addition, their ability to grasp and hang on the wire with all four paws for at least 5 seconds and to climb back on the wire is determined Quantification of Vascular Amyloid Deposition For quantification of cerebral amyloid angiopathy (CAA), 5 µm paraffin-embedded sections at 30 µm intervals through the parietal or cerebellar cortex leptomeninges are immunostained with biotinylated-Ab9 antibody (anti-Aβ1-16, 1:500) overnight at 4° C. (n=5-7 mice per genotype at each age group, n=6 sections per mouse). Positively stained blood vessels are visually assessed using modified Vonsattel's scoring system (48) The CAA severity score is calculated by multiplying the number of CAA vessels with the CAA severity grade.

Histology: Immunohistochemistry and Immunofluorescence

Tg and WT mice from 3 to 12 months are anesthetized and transcardially perfused sequentially with 0.9% NaCl and 4% paraformaldehyde in 0.1 mol/L phosphatebuffered saline (PBS) (pH 7.4) or 10% formalin and 4% paraformaldehyde in 0.1 mol/L PBS (pH 7.4). Brains and spinal cords are removed and stored in 4% paraformaldehyde. Some samples are embedded in paraffin and cut on a sliding microtome at a thickness of 10 µm. Cryosections (14 µm) are cut on a cryostat and mounted on chrome alum-coated slides. Endogenous peroxidase is quenched by treating the section with methanol containing 0.3% H2O2 for 30 minutes. Sections are blocked in 10% horse serum. Primary antibodies are used and incubated overnight at 4° C. in the presence of 1% horse serum. All secondary biotinylated or fluorescein-, Texas Red-, and AMCA-coupled antibodies, fluorochromes, ABC-kit, and 3,3'-diaminobenzidine as chromogen for peroxidase activity are from Vector Laboratories. Incubation with the secondary antibody is held at room temperature for 1 hour. All washing steps (3-10 minutes) and antibody dilution are performed using phosphate-buffered saline (0.1 mol/L PBS, pH 7.4) or Tris-buffered saline (0.01 mol/L Tris, 0.15 mol/L NaCl, pH 7.4). Incubation with the ABC complex and detection with 3,3'-diaminobenzidine is carried out according to the manufacturer's manual. Hematoxylin counterstaining is performed according to standard procedures. A minimum of three mice per genotype, age, and sex is used for each determination (49).

Preparation of Brain Extracts.

Brains are rapidly harvested over ice between 90 and 120 min after the final injection and frozen to −80° C. The right cerebral hemisphere from each mouse is weighed after freezing. Analysis of hemisphere mass by median absolute deviation allows us to exclude samples that are beyond 4 median absolute deviations from the rest of the set. Cerebral hemispheres are homogenized, and cell lysates containing whole protein are prepared according to the manufacturer's instructions for enzymatic assay kits (R&D Systems, Inc.). In brief, the brain cortices are homogenized in 800 µl of low salt containing 1× extraction buffer (R&D kit) and incubated on ice for 10 min. The homogenates are then centrifuged at 13,000 g for 15 min at 4° C. The protein concentration in each sample is estimated according to biuret-derived assay (Pierce). Levels of APP, Aβ40, and Aβ42 are measured by Western immunoblotting and sandwich ELISA techniques, respectively, as described (41). In addition, activities of α-, β-, and γ-secretases may be measured from the same extracts.

Assay of Levels of Total APP in Mouse Cerebral Cortex Extracts

An equal-protein amount of brain extracts is loaded in each gel, 30 μg per lane per sample. Each gel contained eight treatments: control; drug 1 7.5 mg/kg dose; and drug 2 in several doses. To minimize intra-gel variation, each gel contained three sets of all treatment groups. Each blot is probed with 22C11 antibody. Each blot is also probed with the β-actin antibody for normalization to transfer efficiency. The intensity of APP band signal is normalized with that of β-actin. Two sample "controls" are loaded in each gel/blot to test for blot to blot variation. Analysis of blots is performed in two ways: blot wise (n=3), to test for gel to gel variation; and combined blots (n=9 or 10) as described (50-51). Blot-wise analysis with n=3 shows the same trend as the final analysis with n=9 or 10 does. Results of the combined analysis are presented.

Aβ Sandwich ELISA

For brain Aβ ELISAs, forebrain and hindbrain Aβ levels are determined independently, and the olfactory bulb is excluded from analysis. For plasma Aβ analysis, blood is collected in EDTA-coated tubes after cardiac puncture. Blood samples are centrifuged at 3000 rpm for 10 min at 4° C., and the plasma is aliquoted and stored at −80° C. until used. Aβ levels are determined by end-specific sandwich ELISAs using Ab9 (anti-Aβ1-16 Ab) as the capture Ab for Aβ40, 13.1.1-HRP (anti-Aβ35-40 Ab) as the detection Ab for Aβ40, 2.1.3 (anti-Aβ35-42 Ab) as the capture Ab for Aβ42, and Ab9-HRP as the detection Ab for Aβ42 (n=5-7 mice per genotype at each age group). Aβ levels are normalized to the previous results using the same sets of mice as internal controls to minimize potential ELISA variability, as described (41).

Western Blotting

Snap-frozen forebrain samples are homogenized in radio-immunoprecipitation assay (RIPA) buffer (Boston BioProducts, Worcester, Mass.) with 1% protease inhibitor mixture (Roche). The homogenate is centrifuged at 100,000×g for 1 h at 4° C. Protein concentration in supernatants is determined using the BCA protein assay (Pierce).

Protein samples (20 μg) are run on Bis-Tris 12% XT gels or Bis-Tris 4-12% XT gels (Bio-Rad, Hercules, Calif.) and transferred to 0.2 μm nitrocellose membranes. Blots are microwaved for 2 min in 0.1 M PBS twice and probed with Ab 82E1 (anti-Aβ1-16, 1:1000; IBL, Gunma, Japan) and anti-APP C-terminal 20 amino acids (1:1000) as described (41). Blots are stripped and reprobed with anti β-actin (1:1000; Sigma) as a loading control. Relative band intensity is measured using ImageJ software.

Quantification of Parenchymal Amyloid Deposition

Hemibrains are immersion fixed in 10% formalin and processed for paraffin embedding. Brain tissue sections (5 μm) were immunostained with anti-total Aβ antibody (Ab). Sections are counterstained with hematoxylin. Six sections per brain through the hippocampus, piriform cortex (bregma, −1.70 to −2.80 mm), or cerebellum (paraflocculus, crus ansiform, and simple lobules; bregma, −5.40 to −6.36 mm) are used for quantification (n=5-7 mice per genotype at each age group). The Aβ plaque burden is determined using Meta-Morph software (Molecular Devices, Palo Alto, Calif.). For quantification of cored plaques, serial sections of those analyzed for Aβ burden are stained with thioflavine S (ThioS), and the number of ThioS-positive plaques in the hippocampus, entorhinal/piriform cortex, or the cerebellum is counted. All of the above analyses are performed in a blinded manner.

Statistical Analysis of In Vivo Data.

Results from all experiments are analyzed with STATISTICA 8.0 (Statsoft).

Aβ levels, amyloid plaque burden, and CAA severity are analyzed by using ANOVA with the post hoc Holm-Sidak multiple comparison test or two-tailed Student's t test. If the data set does not meet the parametric test assumptions, either the Kruskal-Wallis test followed by the post hoc Dunn's multiple comparison or the Mann-Whitney rank sum test is performed. To test whether the Aβ levels in the bitransgenic mice were consistent with an additive sum of Aβ levels in the single transgenic littermates, a multiple linear regression with no intercept test is used. All comparisons are made between littermates.

Drug response modelling is done excluding the control (0 mg/kg) samples. ED50 corresponds to the dose (mg/kg) required to induce a 50% of maximal drug-induced response in the experiments. It is calculated using the Hill equation model for the log of ED50.

In vivo experiments are performed for candidate drug combinations. Positive results on, learning and spatial memory are listed in table 7 below.

TABLE 7

| Drug combination | Morris water Maze |
| --- | --- |
| Sulfisoxazole and Levosimendan | + |
| Sulfisoxazole and Terbinafine | + |

Bibliography

1. Crook R., Verkkoniemi A., et al. (1998). A variant of Alzheimer's disease with spastic paraparesis and unusual plaques due to deletion of exon 9 of presenilin 1. *Nat Med.* 4(4): 452-5.
2. Houlden H., Baker M., et al. (2000). Variant Alzheimer's disease with spastic paraparesis and cotton wool plaques is caused by PS-1 mutations that lead to exceptionally high amyloid-beta concentrations. *Ann Neurol.* 48(5): 806-8.
3. Kwok J. B., Taddei K., et al. (1997). Two novel (M233T and R278T) presenilin-1 mutations in early-onset Alzheimer's disease pedigrees and preliminary evidence for association of presenilin-1 mutations with a novel phenotype. *Neuroreport.* 8(6): 1537-42.
4. Verkkoniemi A., Kalimo H., et al. (2001). Variant Alzheimer disease with spastic paraparesis: neuropathological phenotype. *J Neuropathol Exp Neurol.* 60(5): 483-92.
5. Citron M. (2004). Strategies for disease modification in Alzheimer's disease. *Nat Rev Neurosci.* 5(9): 677-85.
6. Suh Y. H. and Checker F. (2002). Amyloid precursor protein, presenilins, and alpha-synuclein: molecular pathogenesis and pharmacological applications in Alzheimer's disease. *Pharmacol Rev.* 54(3): 469-525.
7. Blacker D., Albert M. S., et al. (1994). Reliability and validity of NINCDS-ADRDA criteria for Alzheimer's disease. The National Institute of Mental Health Genetics Initiative. *Arch Neurol.* 51(12): 1198-204.
8. Rossor M. N., Fox N. C., et al. (1996). Clinical features of sporadic and familial Alzheimer's disease. *Neurodegeneration.* 5(4): 393-7.
9. Glenner G. G., Wong C. W., et al. (1984). The amyloid deposits in Alzheimer's disease: their nature and pathogenesis. *Appl Pathol.* 2(6): 357-69.

10. Ballatore C., Lee V. M., et al. (2007). Tau-mediated neurodegeneration in Alzheimer's disease and related disorders. *Nat Rev Neurosci.* 8(9): 663-72.
11. Bell K. F. and Claudio Cuello A. (2006). Altered synaptic function in Alzheimer's disease. *Eur J Pharmacol.* 545(1): 11-21.
12. Hardy J. A. and Higgins G. A. (1992). Alzheimer's disease: the amyloid cascade hypothesis. *Science.* 256(5054): 184-5.
13. Braak H. and Braak E. (1991). Neuropathological staging of Alzheimer-related changes. *Acta Neuropathol.* 82(4): 239-59.
14. Golde T. E. (2005). The Abeta hypothesis: leading us to rationally-designed therapeutic strategies for the treatment or prevention of Alzheimer disease. *Brain Pathol.* 15(1): 84-7.
15. Hardy J. and Selkoe D. J. (2002). The amyloid hypothesis of Alzheimer's disease: progress and problems on the road to therapeutics. *Science.* 297(5580): 353-6.
16. Selkoe D. J. (2000). The genetics and molecular pathology of Alzheimer's disease: roles of amyloid and the presenilins. *Neurol Clin.* 18(4): 903-22.
17. Gorlach A., Klappa P., et al. (2006). The endoplasmic reticulum: folding, calcium homeostasis, signaling, and redox control. *Antioxid Redox Signal.* 8(9-10): 1391-418.
18. Verkhratsky A. (2004). Endoplasmic reticulum calcium signaling in nerve cells. *Biol Res.* 37(4): 693-9.
19. Copanaki E., Schürmann T., et al. (2007). The amyloid precursor protein potentiates CHOP induction and cell death in response to ER Ca2+ depletion. *Biochim Biophys Acta.* 1773 (2): 157-65.
20. Chan S. L., Mayne M., et al. (2000). Presenilin-1 mutations increase levels of ryanodine receptors and calcium release in PC12 cells and cortical neurons. *J Biol. Chem.* 275(24): 18195-200.
21. Supnet C., Grant J., et al. (2006). Amyloid-beta-(1-42) increases ryanodine receptor-3 expression and function in neurons of TgCRND8 mice. *J Biol Chem.* 281(50): 38440-7.
22. Guo Q., Fu W., et al. (1999). Increased vulnerability of hippocampal neurons to excitotoxic necrosis in presenilin-1 mutant knock-in mice. *Nat Med.* 5(1):101-6.
23. LaFerla F. M. (2002). Calcium dyshomeostasis and intracellular signalling in Alzheimer's disease. *Nat Rev Neurosci.* 3(11): 862-72.
24. Wong H. K., Sakurai T., et al. (2005). β-Subunits of voltage-gated sodium channels are novel substrates of beta-site amyloid precursor protein-cleaving enzyme (BACE1) and γ-secretase. *J Biol Chem.* 280(24):23009-17.
25. Lippa C. F., Schmidt M. L., et al. (1999). Antibodies to alpha-synuclein detect Lewy bodies in many Down's syndrome brains with Alzheimer's disease. *Ann Neurol.* 45(3): 353-7.
26. Hamilton R. L. (2000). Lewy bodies in Alzheimer's disease: a neuropathological review of 145 cases using alpha-synuclein immunohistochemistry. *Brain Pathol.* 10(3): 378-84.
27. Morelli L., Llovera R., et al. (2003). Differential degradation of amyloid beta genetic variants associated with hereditary dementia or stroke by insulin-degrading enzyme. *J Biol Chem.* 278(26):23221-6
28. Lee D. S., Tomita S., et al. (2000). Regulation of X11L-dependent amyloid precursor protein metabolism by XB51, a novel X11L-binding protein. *J Biol Chem.* 275 (30): 23134-8.
29. Mueller H. T., Borg J. P., et al. (2000). Modulation of amyloid precursor protein metabolism by X11 alpha/Mint-1. A deletion analysis of protein-protein interaction domains. *J Biol Chem.* 275(50): 39302-6.
30. Cookson M. R. (2003). Neurodegeneration: how does parkin prevent Parkinson's disease? *Curr Biol.* 13(13): R522-4.
31. Mazanetz M. P. and Fischer P. M. (2007). Untangling tau hyperphosphorylation in drug design for neurodegenerative diseases. *Nat Rev Drug Discov.* 6(6): 464-79.
32. Churcher I. (2006). Tau therapeutic strategies for the treatment of Alzheimer's disease. *Curr Top Med Chem.* 6(6): 579-95.
33. Sze C. I., Su M., et al. (2004). Down-regulation of WW domain-containing oxidoreductase induces Tau phosphorylation in vitro. A potential role in Alzheimer's disease. *J Biol Chem.* 279(29): 30498-506.
34. Wälchli S., Curchod M. L., et al. (2000). Identification of tyrosine phosphatases that dephosphorylate the insulin receptor. A brute force approach based on "substrate-trapping" mutants. *J Biol Chem.* 275(13):9792-6.
35. Chang N. S., Doherty J., et al. (2003). JNK1 physically interacts with WW domain-containing oxidoreductase (WOX1) and inhibits WOX1-mediated apoptosis. *J Biol Chem.* 278(11):9195-202.
36. D'Orazi G., Cecchinelli B., et al. (2002). Homeodomain-interacting protein kinase-2 phosphorylates p53 at Ser 46 and mediates apoptosis. *Nat Cell Biol.* 4(1):11-9.
37. Zhu H., Wu L., et al. (2003). MDM2 and promyelocytic leukemia antagonize each other through their direct interaction with p53. *J Biol Chem.* 278(49):49286-92.
38. Rodrigues S., De Wever O., et al. (2007). Opposing roles of netrin-1 and the dependence receptor DCC in cancer cell invasion, tumor growth and metastasis. *Oncogene.* 26(38): 5615-25.
39. Arakawa H. (2004). Netrin-1 and its receptors in tumorigenesis. *Nat Rev Cancer.* 4(12):978-87.
40. Taniguchi Y., Kim S. H., et al. (2003). Presenilin-dependent "gamma-secretase" processing of deleted in colorectal cancer (DCC). *J Biol Chem.* 278(33):30425-8.
41. Lahiri D. K. et al. (2007) Experimental Alzheimer's Disease Drug Posiphen [(Phenserine] Lowers Amyloid-betaPeptide Levels in Cell Culture and Mice. Journal of Pharmacology and experimental therapeutics 320: 386-396.
42. Sang Tae K I M, et al. (2006) Neuroprotective Effect of Some Plant Extracts in Cultured CT105-Induced PC12 Cells. *Biol. Pharm. Bull.* 29(10) 2021-2024
43. McGowan E., et al. (2005) Aβ42 Is Essential for Parenchymal and Vascular Amyloid Deposition in Mice. Neuron 47: 191-199.
44. Leighty R. E. et al. (2008) Use of artificial neural networks to determine cognitive impairment and therapeutic effectiveness in Alzheimer's transgenic mice. Journal of Neuroscience Methods 167: 358-366
45. Ashe K H (2001) Learning and memory in transgenic mice modelling Alzheimer's disease. Learning and Memory 8: 301-308.
46. Carlson G A, et al. (1997) Genetic modification of the phenotypes produced by amyloid precursor protein overexpression in transgenic mice. Human Molecular Genetics 6:1951-1959.
47. Hsiao K, et al. (1996) Correlative memory deficits, Abeta elevation, and amyloid plaques in transgenic mice. Science 274: 99-102.
48. Greenberg S. M. and Vonsattel J. P. (1997) Diagnosis of cerebral amyloid angiopathy. Sensitivity and specificity of cortical biopsy. Stroke 28(7):1418-22
49. Schindowski K. et al. (2006) Alzheimer's Disease-Like Tau Neuropathology Leads to Memory Deficits and Loss of Functional Synapses in a Novel Mutated Tau Transgenic Mouse without Any Motor Deficits. Am J Pathol. 169: 599-616.
50. Lahiri D K, et al. (2004) Dietary supplementation with melatonin reduces levels of amyloid beta-peptides in the murine cerebral cortex. *Journal of Pineal Research* 36:224-231.
51. Basha M R, et al. (2005) The fetal basis of amyloidogenesis: exposure to lead and latent overexpression of amyloid precursor protein and beta-amyloid in the aging brain. *Journal of Neuroscince* 25: 823-829.
52. Miyakawa T: Electron microscopy of amyloid fibrils and microvessels. (1997) Ann NY Acad Sci 826: 25-34.
53. Smith E E, Greenberg S M. Beta-amyloid, blood vessels, and brain function. Stroke. (2009) 40(7):2601-6.
54. Paris D, Ait-Ghezala G, Mathura V S, Patel N, Quadros A, Laporte V, Mullan M. Anti-angiogenic activity of the mutant Dutch A(beta) peptide on human brain microvascular endothelial cells. Brain Res Mol Brain Res. 2005 20; 136(1-2):212-30.

The invention claimed is:

1. A method of treating Alzheimer's disease, the method comprising administering to a subject in need thereof an effective amount of sulfisoxazole, or a salt, prodrug, or sustained release formulation thereof.

2. The method of claim 1, further comprising simultaneously, separately, or sequentially administering to the subject at least one additional compound chosen from the group consisting of acamprosate, amlodipine, cilostazol, leflunomide, levosimendan, methimazole, phenformin, prilocaine, tadalafil, terbinafine, zonisamide, and rifabutin, or salts, prodrugs, or sustained release formulations thereof.

* * * * *